(12) United States Patent
Kumagai et al.

(10) Patent No.: US 6,989,986 B2
(45) Date of Patent: Jan. 24, 2006

(54) PLANE UNIT STRUCTURE

(75) Inventors: Minoru Kumagai, Kawasaki (JP); Koichi Inoue, Kawasaki (JP); Masuo Ohnishi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 191 days.

(21) Appl. No.: 10/754,482

(22) Filed: Jan. 8, 2004

(65) Prior Publication Data
US 2004/0184224 A1 Sep. 23, 2004

Related U.S. Application Data

(63) Continuation of application No. PCT/JP02/03463, filed on Apr. 5, 2002.

(30) Foreign Application Priority Data

Jul. 10, 2001 (JP) .................................. 2001-209740

(51) Int. Cl.
*G06F 1/16* (2006.01)

(52) U.S. Cl. .................... 361/681; 361/683; 248/917; 349/58

(58) Field of Classification Search ......... 361/680–685, 361/687, 688; 349/58–62, 16, 70, 65, 158, 349/165; 248/917–919, 921–923; 345/905; 359/83, 811, 819; 364/708.1; 312/223.1, 312/223.2; 40/530; 385/146
See application file for complete search history.

(56) References Cited

U.S. PATENT DOCUMENTS

| | | | | |
|---|---|---|---|---|
| 5,379,182 A | * | 1/1995 | Fujimori et al. | 361/681 |
| 5,872,606 A | * | 2/1999 | Kim | 349/58 |
| 5,946,061 A | * | 8/1999 | Kurihara et al. | 349/58 |
| 6,064,565 A | * | 5/2000 | Ishihara et al. | 361/681 |
| 6,128,183 A | * | 10/2000 | Uchiyama et al. | 361/681 |
| 6,212,067 B1 | * | 4/2001 | Nakajima et al. | 361/681 |
| 6,233,140 B1 | * | 5/2001 | Cummings et al. | 361/683 |
| 6,330,148 B1 | * | 12/2001 | Won et al. | 361/681 |
| 6,389,643 B1 | * | 5/2002 | Lim et al. | 16/271 |
| 6,392,724 B2 | * | 5/2002 | An et al. | 349/58 |
| 6,411,501 B1 | * | 6/2002 | Cho et al. | 361/681 |
| 6,525,790 B1 | * | 2/2003 | Kan-o | 349/58 |
| 6,611,302 B1 | * | 8/2003 | Ueda et al. | 349/58 |
| 6,618,240 B1 | * | 9/2003 | Kim | 361/681 |
| 6,636,282 B2 | * | 10/2003 | Ogawa et al. | 349/58 |
| 6,741,298 B1 | * | 5/2004 | Won | 349/58 |
| 6,747,713 B1 | * | 6/2004 | Sato | 349/58 |
| 2001/0038523 A1 | | 11/2001 | Bang | |
| 2003/0063230 A1 | * | 4/2003 | Kato et al. | 349/58 |

FOREIGN PATENT DOCUMENTS

| | | |
|---|---|---|
| JP | 5-150224 | 6/1993 |
| JP | 5-150225 | 6/1993 |
| JP | 5-73790 | 10/1993 |
| JP | 3051361 | 6/1998 |
| JP | 11-85319 | 3/1999 |
| JP | 11-184392 | 7/1999 |
| JP | 11-190974 | 7/1999 |
| JP | 11-298157 | 10/1999 |
| JP | 2000-19978 | 1/2000 |
| JP | 2000-181371 | 6/2000 |
| JP | 2000-250014 | 9/2000 |
| JP | 2001-027912 | 1/2001 |
| JP | 2001-083887 | 3/2001 |

* cited by examiner

*Primary Examiner*—Michael Datskovsky
(74) *Attorney, Agent, or Firm*—Greer, Burns & Crain, Ltd.

(57) ABSTRACT

Information processing apparatus, particularly a plane display unit used both for a display and an inputting device is required to be small-sized when it is attached to a housing. For this purpose, a flat rectangular plane display unit is attached to the housing by means of fixing members at three positions; left and right sides and an upper central positions. The left and right sides of the plane display unit are fixed to a back cover with screws using the fixing members and the upper central position of the plane display unit is clamped by the fixing member to be fixed to the housing.

42 Claims, 19 Drawing Sheets

ENLARGED VIEW OF A

ENLARGED VIEW OF B

CROSS-SECTIONAL VIEW OF E-E

CROSS-SECTIONAL VIEW OF F-F

CROSS-SECTIONAL VIEW OF G-G

Fig.23
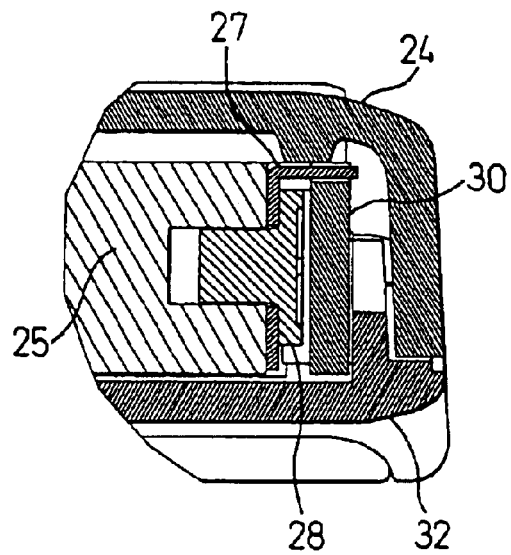
CROSS-SECTIONAL VIEW OF H-H
Fig.24
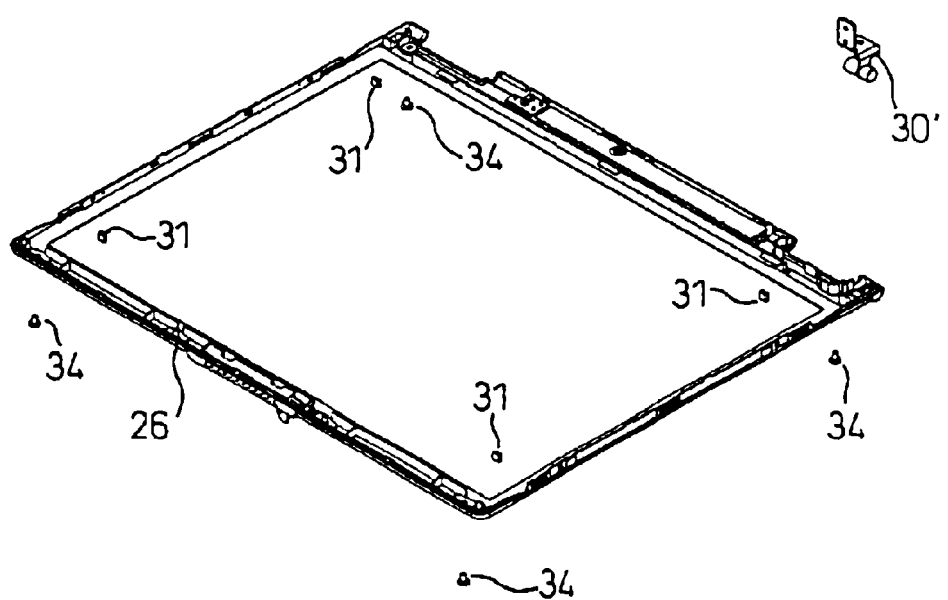

PLANE UNIT STRUCTURE

CROSS-REFERENCE TO RELATED APPLICATIONS

This application is based upon and claims priority of Japanese Patent Application No. 2001-209740, filed on Jul. 10, 2001, the contents being incorporated herein by reference, and is a continuation of PCT/JP02/03463 filed Apr. 5, 2002.

TECHNICAL FIELD

The present invention relates to a plane unit structure, particularly to an information processing apparatus having a display unit, and to an attachment structure for attaching a plane display unit to a housing of the information processing apparatus.

The information processing apparatus is required to be small-sized and light-weighted. Particularly, the plane display unit used both for a display and an inputting device is required to be small-sized when it is assembled to the housing.

BACKGROUND ART

In the prior art, the information apparatus such as a word processor or a personal computer of a portable type or a notebook type (hereinafter referred to as a computer) includes a main body having an inputting device such as a keyboard and a display adapted to be openable/closable to the main body, and a plane display unit is often used as the display. The plane display unit is fixed to a housing constituting a cover.

In the prior art, the plane display unit is generally fixed to the housing by using fastening means such as screws at four corners of a rectangular plane display unit. According to such a structure, a space is necessary for disposing the screws between the inside of the housing forming the cover and a side surface of the rectangular plane display unit, which results in the difficulty in the small-sizing of the apparatus.

Also, in the notebook type computer, it is required that the computer is as thin as possible when the display is closed to the main body. Accordingly, not only the main body but also the display should be as thin as possible. Thus, a space between the plane display unit and the housing must be as small as possible in the thickness direction. For this reason, it is unfavorable to provide fastening members such as bolts in a space between the rear side of the plane display unit and the housing or between an upper edge surface or a side edge surface of the plane display unit and a wall portion of the housing.

DISCLOSURE OF THE INVENTION

While the information processing apparatus is required to be small-sized and light-weighted, the plane display unit used both for the display and the inputting device is particularly demanded to be small-sized when assembled to the housing. To achieve such a demand, it is desired to reduce a space as much as possible between the plane display unit and the housing when the plane display unit is assembled to the housing.

To solve the above problem, according to the present invention, a plane unit structure for fastening a rectangular plane unit to a housing at three position left and right side edges and an upper central edge; is provided, wherein side fixing members are fixed to left and right edge surfaces of the plane unit with screws, and wherein the side fixing members are fixed to the housing with screws and the upper central edge of the plane unit is fastened to the housing while being sandwiched between back and front surfaces thereof. According to the present invention, since the structure is provided, wherein the left and right edges of the rectangular plane display unit are fixed to the housing with screws and the upper central edge thereof is fastened to the housing while being sandwiched between back and front surfaces thereof, there is no need for providing a special space between the plane display unit and the housing for fixing the plane display unit, whereby the apparatus could be small-sized.

The back surface of the upper central edge of the plane unit is brought into contact with sheets fixed to the housing, and the front surface thereof is brought into contact with claws of the upper center fixing member fixed to the housing, so that the upper central edge is fixed between the both in a sandwiched manner. Since the upper central edge of the plane display unit is sandwiched between the sheets and the claws, the position between the back and front surfaces of the plane display unit is conveniently regulated.

The sheet is formed of an elastic member. Thereby, the upper central edge of the plane display unit is elastically held and fastened between the sheets and the claws.

The upper center fixing member is provided with a hook portion of a portable type computer comprising a main body and a display having a plane unit openable/closable relative to the main body so that when the display is closed relative to the main body, the display is engaged with the main body by the engagement of the hook portion in the display with an engagement portion in the main body. In this case, since the display and the main body of the portable type computer are engaged with each other while using the fixing member in the upper central area of the plane display unit, it is possible to reduce the number of parts in the apparatus as a whole.

The hook portion has an opening formed in the upper center fixing member, and the display is engaged with the main body by the engagement of the opening with a claw portion defining the engagement portion in the main body.

The upper center fixing member has fixing holes at two positions apart from each other in the direction parallel to the upper edge of the plane unit and fixed to the housing with screws through the fixing holes.

The claws are provided at two positions apart from each other in the direction parallel to the upper edge of the plane unit, and the hook portion is formed between the two claws.

The sheets are provided at two positions opposite to the two claws, respectively.

The side fixing member is an L-shaped member comprising a strip portion extending along each of left and right edge surfaces of the plane unit and a flat proximal end portion which is part of the strip portion exceeding the lower end of each of the left and right edge surfaces and bending from the strip portion at a right angle.

The strip portion of the side fixing member is fixed to each of the left and right edge surfaces with screws at a plurality of positions along each of the left and right edge surface, and the flat portion is fixed to the housing with a screw at one position.

The side fixing member is made of metal having the elasticity.

A distal end portion of the side fixing member opposite to the proximal end portion is apart from each of the left and right edge surfaces of the plane unit and brought into elastic contact with an inner wall surface of the housing.

A shock absorbing member is provided between the strip portion of the side fixing member and the inner wall of the housing.

The shock absorbing member is made of metal having the elasticity.

Also, according to the present invention, A portable type computer comprising a main body and a display which is a plane unit openable/closable relative to the main body is provided, wherein the display comprises a housing and a rectangular plane unit, and side fixing members are fixed to left and right edge surfaces of the plane unit, respectively, with screws, and wherein the side fixing members are fixed to the housing with screws and an upper central edge of the plane unit is fixed to the housing while front and back surfaces thereof are sandwiched.

The display is provided with a frame-like front cover mounted along the outer periphery of the rectangular plane unit to sandwich the plane unit between the front cover and the housing.

A plurality of ribs are provided integral with the plane unit between the upper edge surface of the plane unit and the inner wall surface of the housing along the upper surface of the plane unit.

Further, according to the present invention, a plane unit structure for fixing a rectangular plane unit while sandwiching opposite surfaces thereof in the thickness direction between a front cover and a back cover is provided, wherein fittings are attached to side surfaces of the plane unit with screws and cushion members are brought into contact with the fittings so that the upper and lower surfaces or the left and right side surfaces of the plane unit are fixed to the cover via the cushion members.

Two of the fittings are attached to the left and right side surfaces of the plane unit, respectively.

The fitting is formed of a strip having a width approximately equal to a thickness of the plane unit, which strip has a pair of bending portions at opposite ends thereof bent to be in contact with the upper or lower surface of the plane unit.

Two of the cushion members are adhered to the fitting fixed to the side surface of the plane unit at positions in the vicinity of opposite ends of the fitting in the lengthwise direction thereof, and further two of the cushion members are disposed at positions outside of the pair of bending positions.

The fitting the fitting is fixed to the side surface of the plane unit with screws at two positions in the vicinity of lengthwise ends thereof, and the cushion members are adhered to the fitting at an end position closer to the screw-fixed position.

The fitting has second bending portions at positions on one side in the widthwise direction bent away from the plane unit, and wherein these second bending portions are provided at opposite ends except for a central area in the lengthwise direction of the fitting, to be brought into contact with ribs provided in the front cover when the plane unit is sandwiched between the front and back covers.

A pair of hinge arms are fixed to left and right sides of the front cover with screws, and the cushion members are interposed between the fitting fixed to the side surface of the plane unit and hinge arm.

The hinge arm is fixed to a standing-up wall provided along the periphery of the rectangular frame-like front cover at front and back two positions with screws.

Furthermore, according to the present invention, a portable type computer comprising a main body and a display provided with a plane unit openable/closable relative to the main body is provided; the display comprising a rectangular plane unit, opposite surfaces of which are sandwiched between front and back covers as seen in the thickness direction, wherein fittings are attached to side surfaces of the plane unit, and cushion members are provided to be in contact with the fittings so that the upper or lower surface or the left or right surface of the plane unit is fixed to the cover.

A pair of hinge arms are fixed to left and right sides of the front cover with screws, and the cushion member is interposed between the fitting fixed on the side surface of the plane unit and the hinge arm, and wherein a proximal end portion of the hinge is fixed to the main body of the apparatus so that the display is openable/closable relative to the main body of the display.

A pair of hinges are provided on opposite sides of the plane display unit, and each of the hinges is fixed to the main body with a screw on one hand, and to the front or back cover on the other hand, so that the plane display unit is openable/closable relative to the main body.

BRIEF DESCRIPTION OF THE DRAWINGS

FIG. 23 is an enlarged sectional view taken along a line H—H in FIG. 19; and

FIG. 24 is an exploded perspective view showing an armless hinge and a front cover in another embodiment of the present invention.

BEST MODE FOR CARRYING OUT THE INVENTION

The present invention will be described below in more detail based on the preferred embodiments with reference to the attached drawings.

Figure 1:
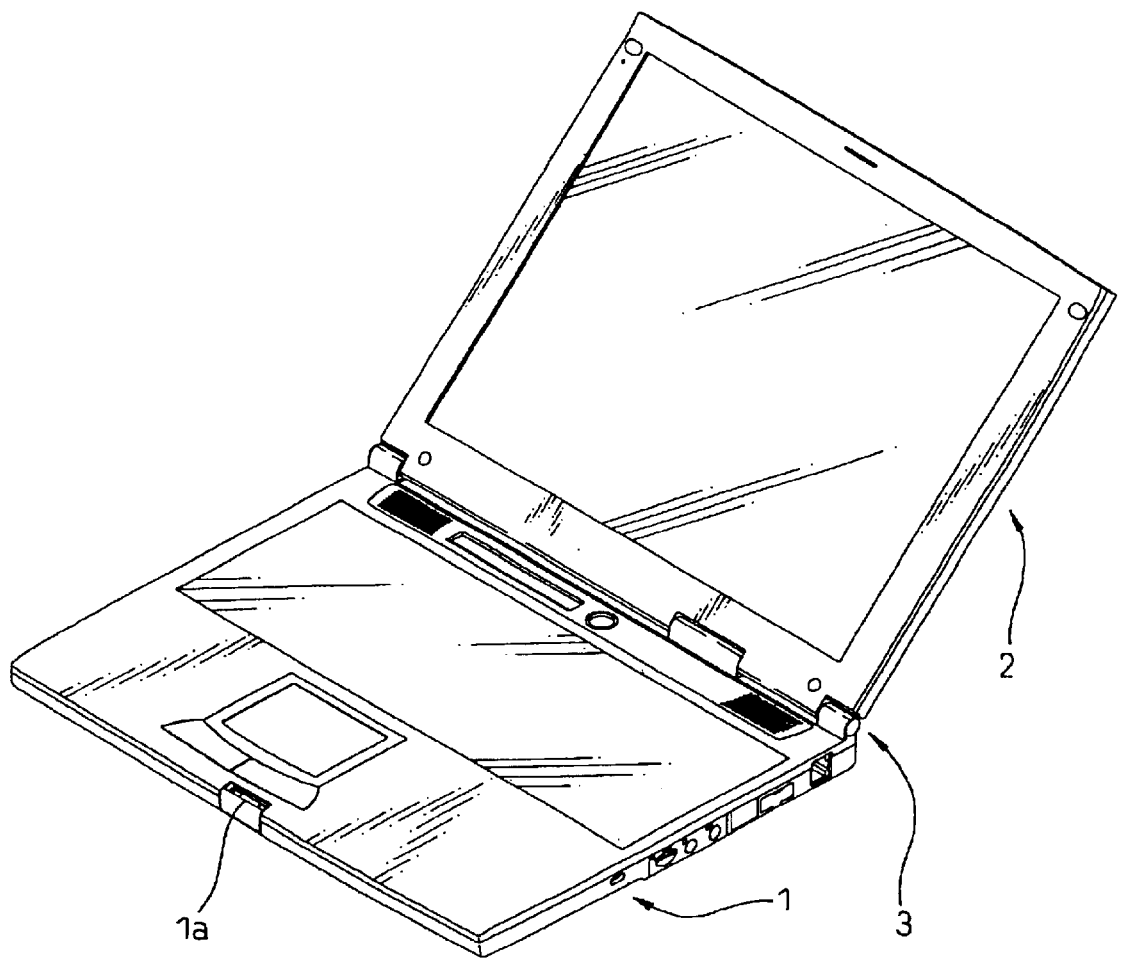
FIG. 1 shows a configuration of the inventive plane unit structure, particularly a portable type computer employing an attachment structure of a plane display unit.

FIG. 1 shows a configuration of the inventive plane unit structure, particularly a portable type computer employing an attachment structure of a plane display unit. The portable type computer includes a main body 1 having a keyboard, a pointer or others, not illustrated in detail, and a display 2 having a plane display unit rotatable about a hinge 3 to be openable and closable to the main body 1. That is, the display 2 is open when the portable type computer is used, and closed when not used.

Next, a first embodiment of the present invention will be described with reference to FIGS. 2 to 11.

Figure 2:
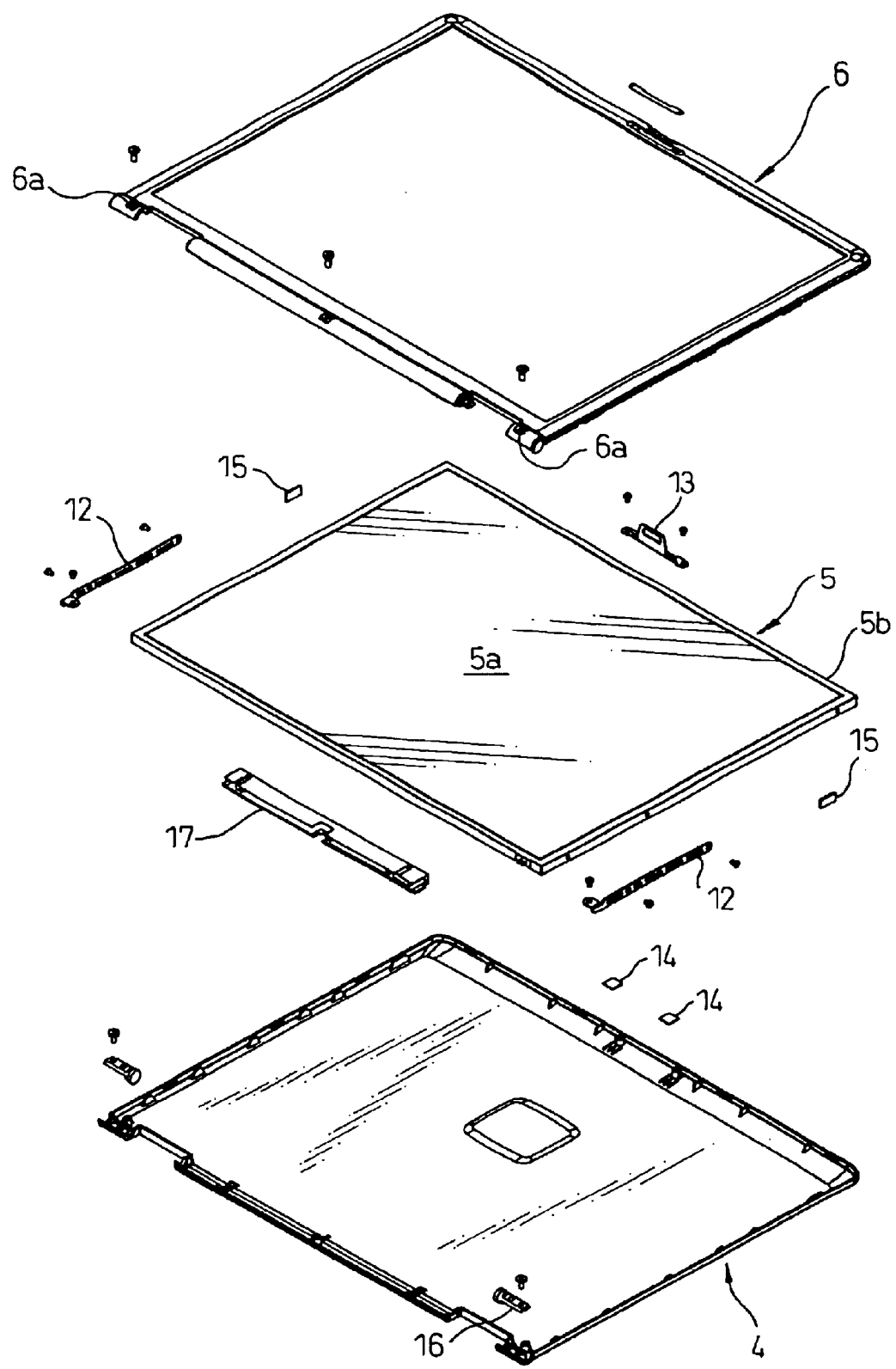
FIG. 2 is an exploded perspective view of a display of a portable type computer employing an attachment structure for a plane display unit according to a first embodiment of the present invention.

FIG. 2 is an exploded perspective view of the display of the portable type computer-showing a first embodiment of the present invention. The display 2 includes a back cover 4 forming a housing, a plane display unit 5 and a front cover 6. As described later, after the plane display unit 5 has been attached to the back cover 4 forming the housing, the front cover 6 is fitted to the periphery of the plane display unit 5.

Figure 3:
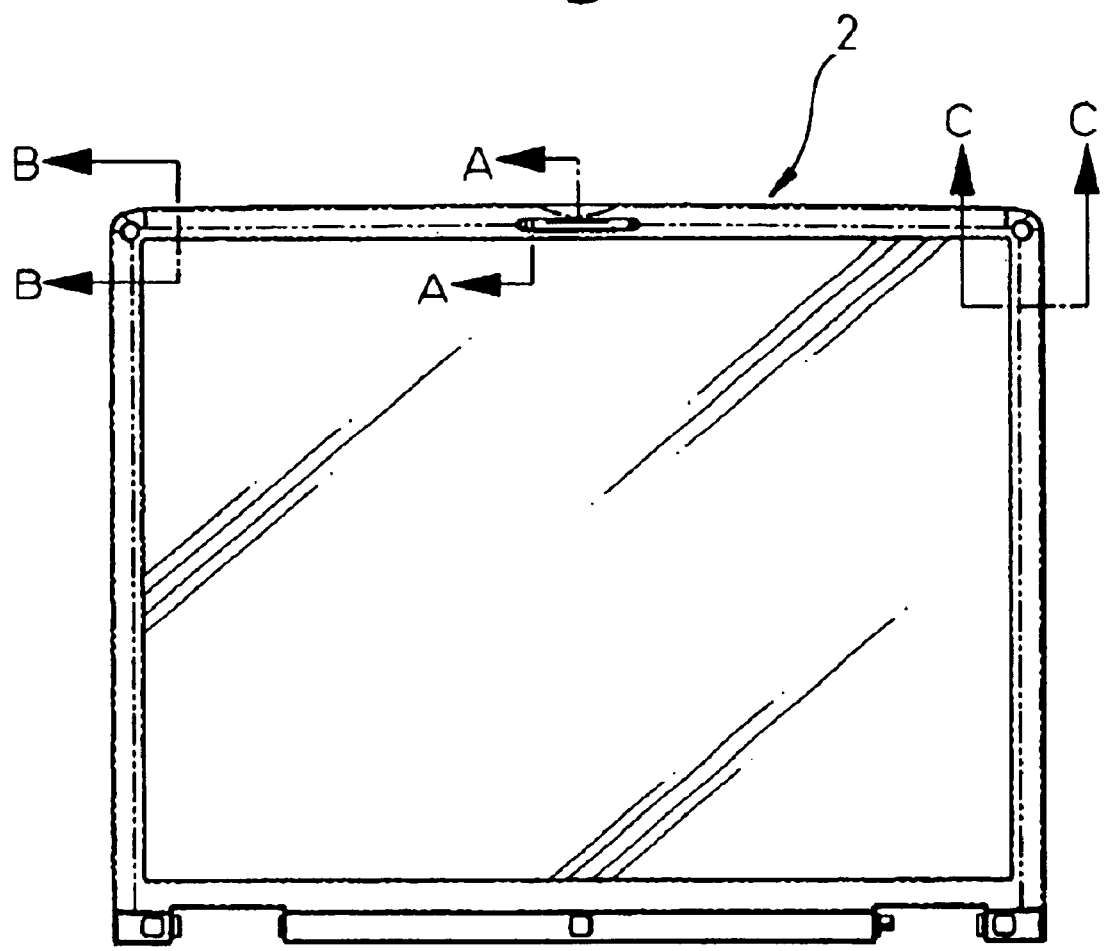
FIG. 3 is a plan view of the display of the portable type computer.
Figure 4A:
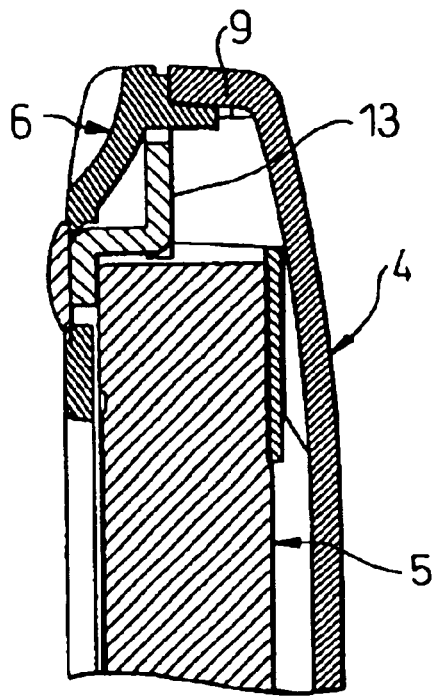
FIGS. 4(a), 4(b) and 4(c) are enlarged sectional views, respectively, taken along lines A—A, B—B and C—C in the display shown in FIG. 3.
Figure 4B:
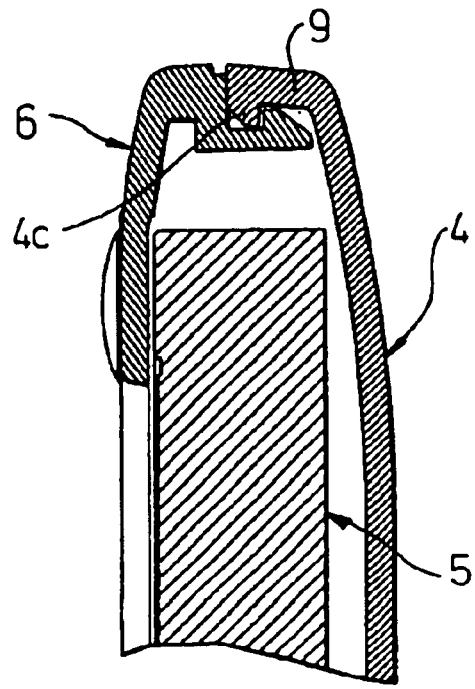
Figure 4C:
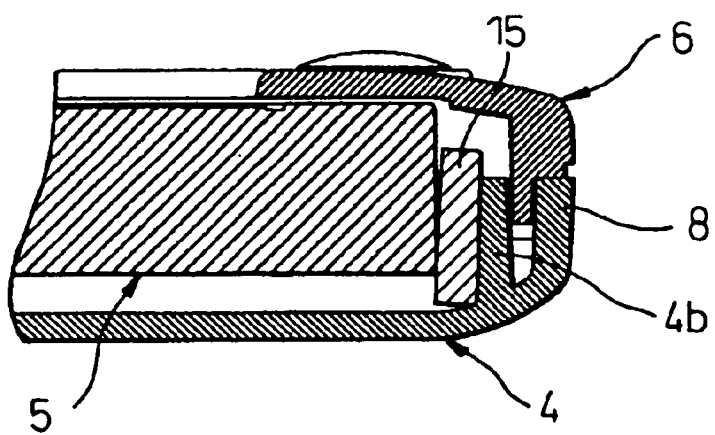

FIG. 3 is a plan view of the display of the portable type computer, in which the back cover 4, the plane display unit 5 and the front cover 6 are assembled together. FIG. 4 are sectional views, respectively, showing portion of the display shown in FIG. 3. The plane display unit 5 is generally of a flat rectangular shape as a whole, in which a liquid crystal display portion 5a occupying almost all the central area thereof is encircled with a frame portion 5b. The frame portion 5b is a portion used for fixing the plane display unit 5.

While the display 2 is formed of the back cover 4, the plane display unit 5 and the front cover 6 as described above, in this description, a hinge 3 side is referred to as a lower portion and a side opposite thereto is referred to as an upper portion when the display 2 is seen in a used state in which the display is open from the main body 1 as shown in FIG. 1, and a back cover 4 side of the plane display unit 5 is referred to as a rear surface and a front cover 6 side is referred to as a front surface.

Figure 5:
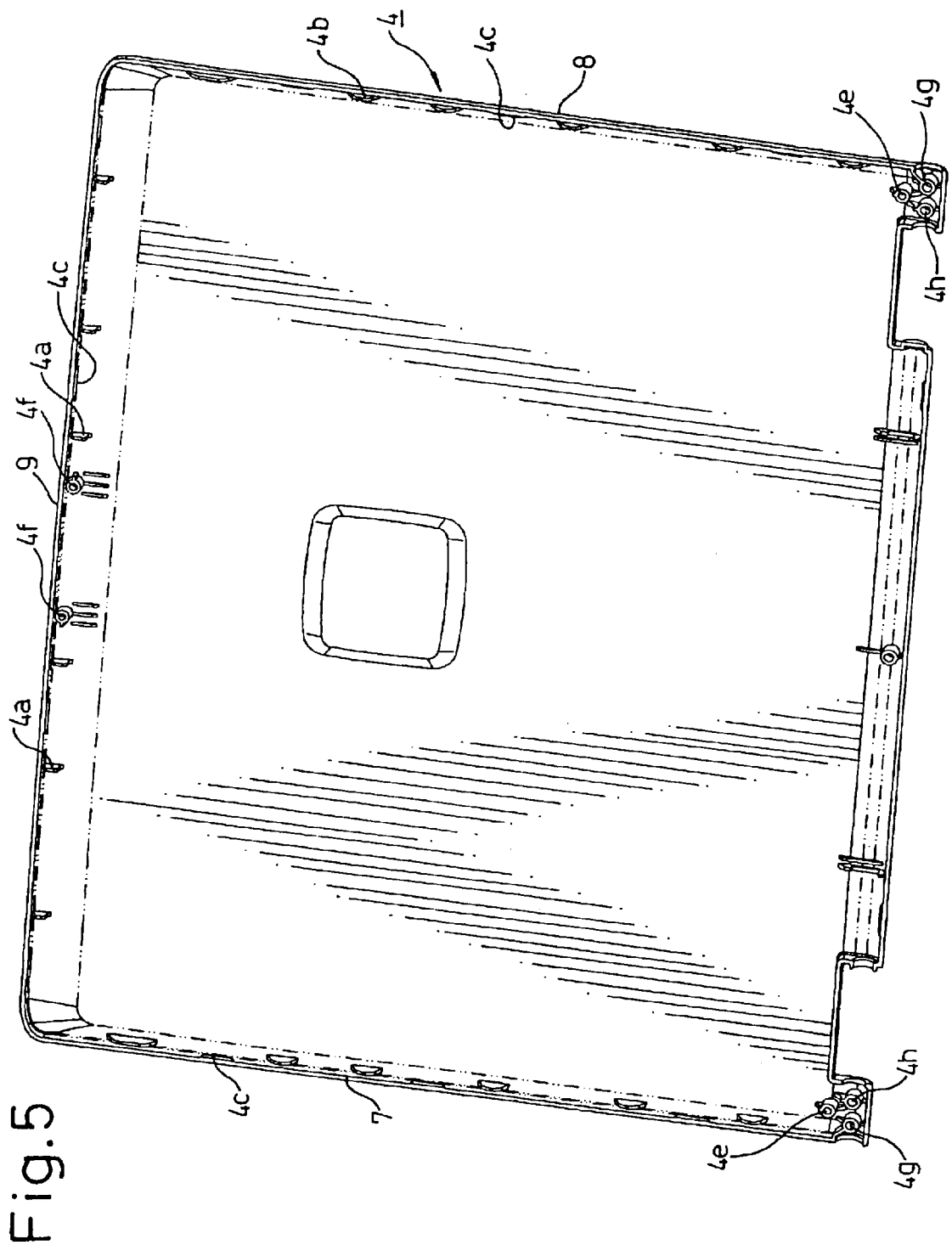
FIG. 5 is a perspective view of a back cover forming a housing of the display.

FIG. 5 is a perspective view of the back cover forming a housing of the display. The back cover 4 is a member to which interior the plane display unit 5 is to be mounted, and the periphery thereof is provided with left and right wall portions 7 and 8 and an upper wall portion 9 standing upward therefrom, except for the lower side on which the hinges are mounted. There are a plurality of claws 4c formed along the inside upper edges of the left and right wall portions 7 and 8 and the upper wall portion 9 to be integral therewith at a distance. There are a plurality of ribs 4a on the inside of the upper wall portion 9 for restricting a gap from the plane display unit 5 as described later, and also there are a plurality of ribs 4b in the left and right wall portions 7 and 8 at a distance between the adjacent ones. In FIG. 5, reference numerals 4e, 4f, 4g and 4h denote screw holes described later. Each of these screw holes is formed in a portion protuberant from a bottom wall of the back cover 4.

The back cover 4 having such a configuration may be prepared as a die cast product, for example, from magnesium alloy.

Figure 6:
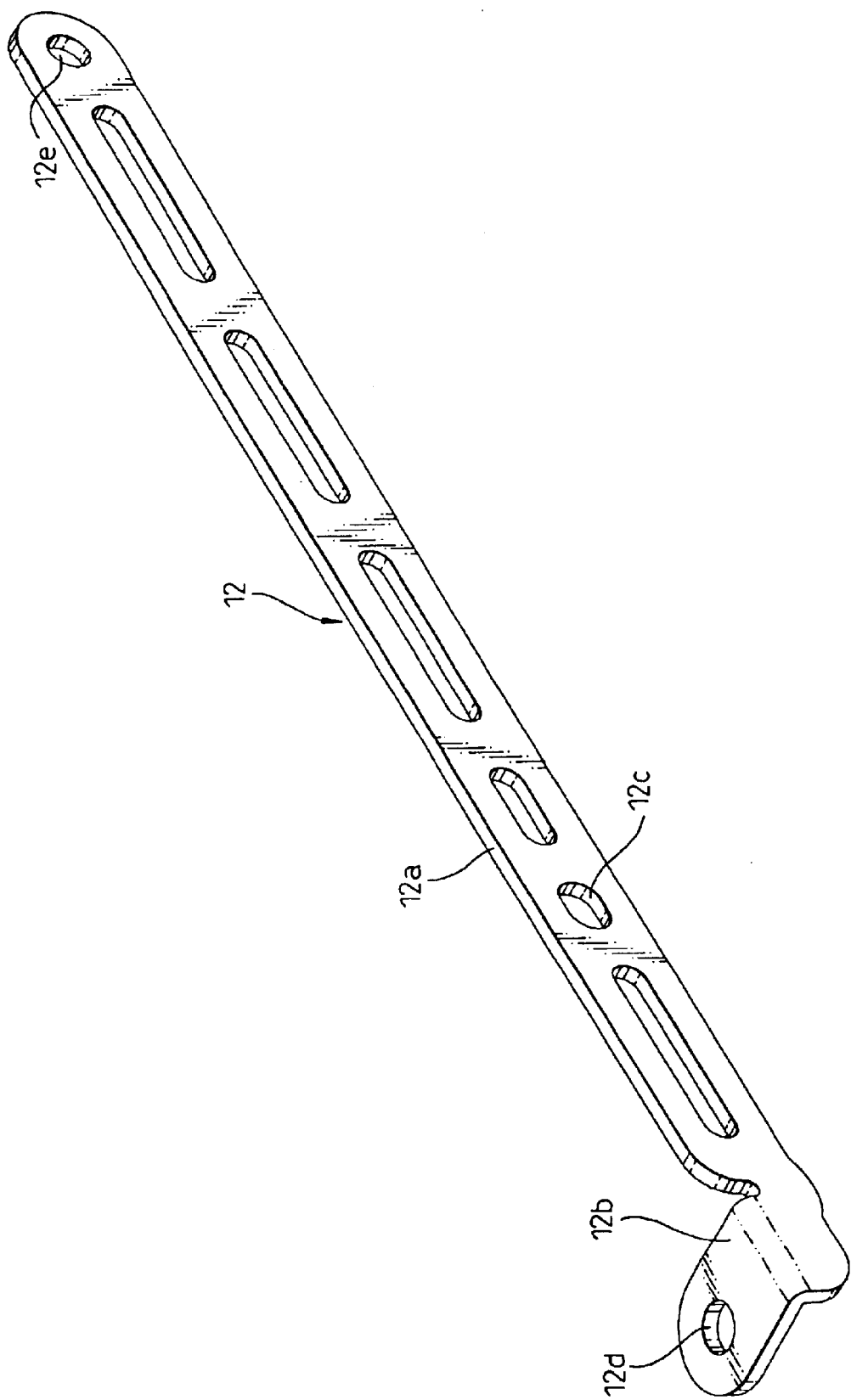
FIG. 6 is a perspective view of a side fixing member for the plane display unit.

FIG. 6 is a perspective view of a side fixing member 12 of the plane display unit 12. This side fixing member 12 is formed of a metallic plate prepared by a sheet metal working as an L-shaped member including, as shown also in FIG. 2, a strip portion 12a extending along each of the left and right edge surfaces of the frame portion 5b in the plane display unit 5 and a flat proximal end portion 12b integral with the former portion, which exceeds the lower end of each the left and right edge surfaces of the frame portion 5b in the plane display unit 5 and is vertically bent from the strip portion 12a. A plurality of holes 12c are provided in the strip portion 12a along the length thereof for inserting screws for fixing the side fixing member to each of the left and right edge surfaces of the frame portion 5b in the plane display unit 5, while a single hole 12d is provided in the proximal end portion 12b for inserting a screw for fixing the side fixing member to the back cover 4 which is a housing. A plurality of openings 12e are provided along the length of the strip portion 12a for reducing a weight of the side fixing member 12 its own.

A pair of left and right side fixing members 12 are used in symmetry with each other. The strip portion 12a of the respective fixing member 12 is fixed onto the respective left or right edge surface of the frame portion 5b in the plane display unit 12, while the proximal end portion 12b is fixed to a screw hole portion of the back cover 4 by a single screw, whereby the side of the plane display unit 5 is fixed to the back cover 4 which is a housing. The side fixing member 12 is made of a metallic material having the elasticity.

In the illustrated embodiment, the side fixing member 12 extends to approximately ⅓ to ½ of the lower area of each the left and right edge surfaces in the liquid crystal display panel 5. In another embodiment, a distal end portion of the side fixing member 12 opposite to the proximal end portion 12b may extend to be away from each of the left and right edge surfaces of the frame portion 5b in the plane display unit 5 and instead elastically in contact with each of the inner wall surfaces 7 and 8.

Figure 7:
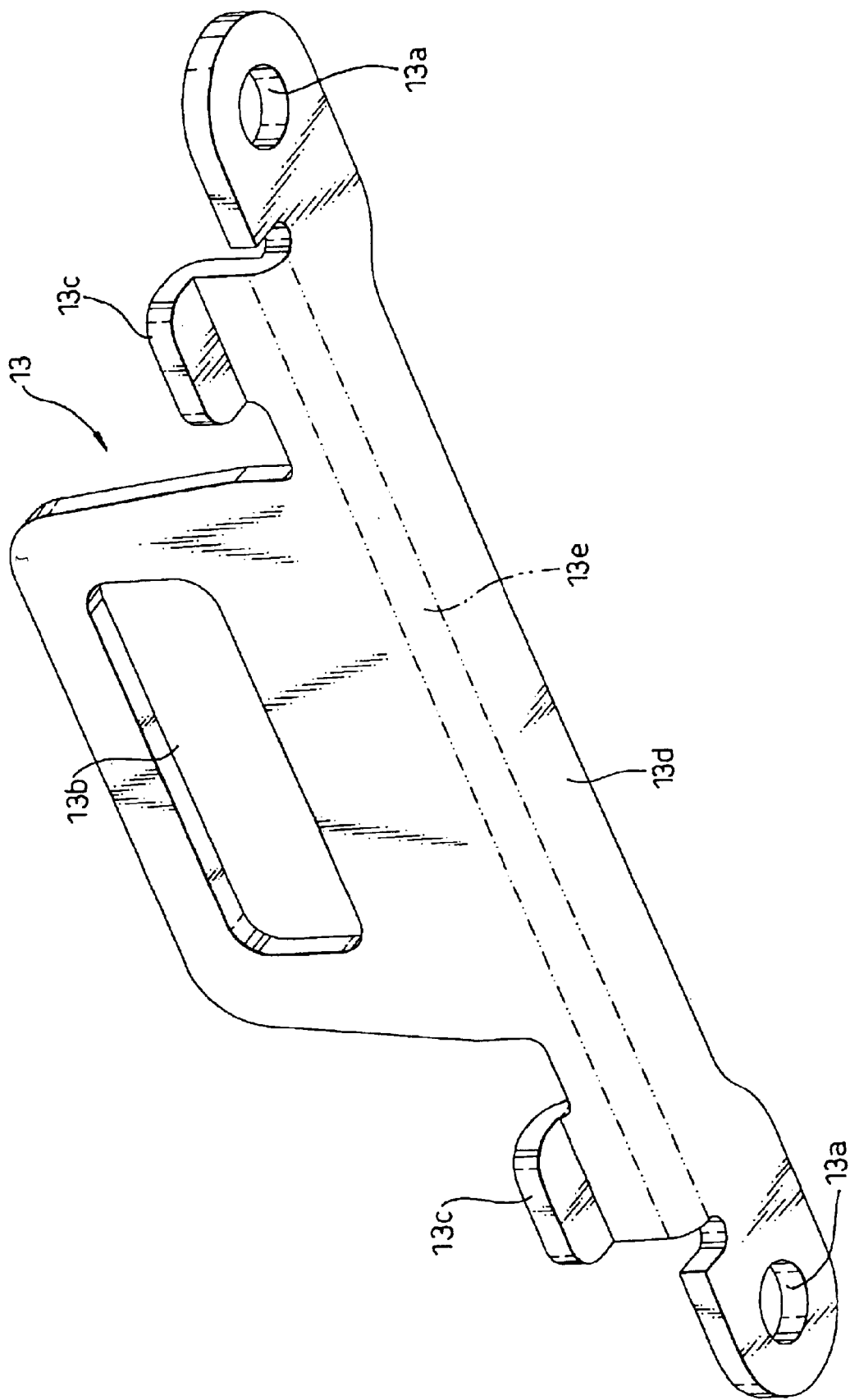
FIG. 7 is a perspective view of a upper center fixing member for the plane display unit.

FIG. 7 is a perspective view of an upper center fixing member 13 for the plane display unit 5. This upper center fixing member 13 is formed of a metallic plate prepared by a sheet metal working to have a proximal portion 13d with a surface generally parallel to the bottom surface of the back cover 4 and extending parallel to the upper edge surface of the plane display unit 5. There are a pair of screw-inserting holes 13a at opposite ends of the proximal portion 13d for fixing the upper center fixing member 13 to the back cover 4.

The upper center fixing member 13 has a central hook portion 13b bent approximately at a right angle from the proximal portion 13d along a lengthwise line 13e, and a pair of claws 13c are formed between the hook portion 13b and the respective screw-inserting holes 13a by further bending them approximately at a right angle.

There is the hook portion 13b in a central area of the upper center fixing member 13. The hook portion 13b has an opening formed in the upper center fixing member 13, which is engaged with a claw 1a (FIG. 1) to fix the display 2 to the main body. That is, when the display 2 is closed to the main body 1, this hook portion 13b in the display 2 is engaged with an engagement portion in the main body 1 to engage the display 2 with the main body 1. When one wishes to open the display 2 from the main body 1, the display 2 is made to rotate relative to the main body 1, whereby the hook portion 13b is disengaged from the engagement portion and the display 2 is open from the main body 1.

Figure 8:
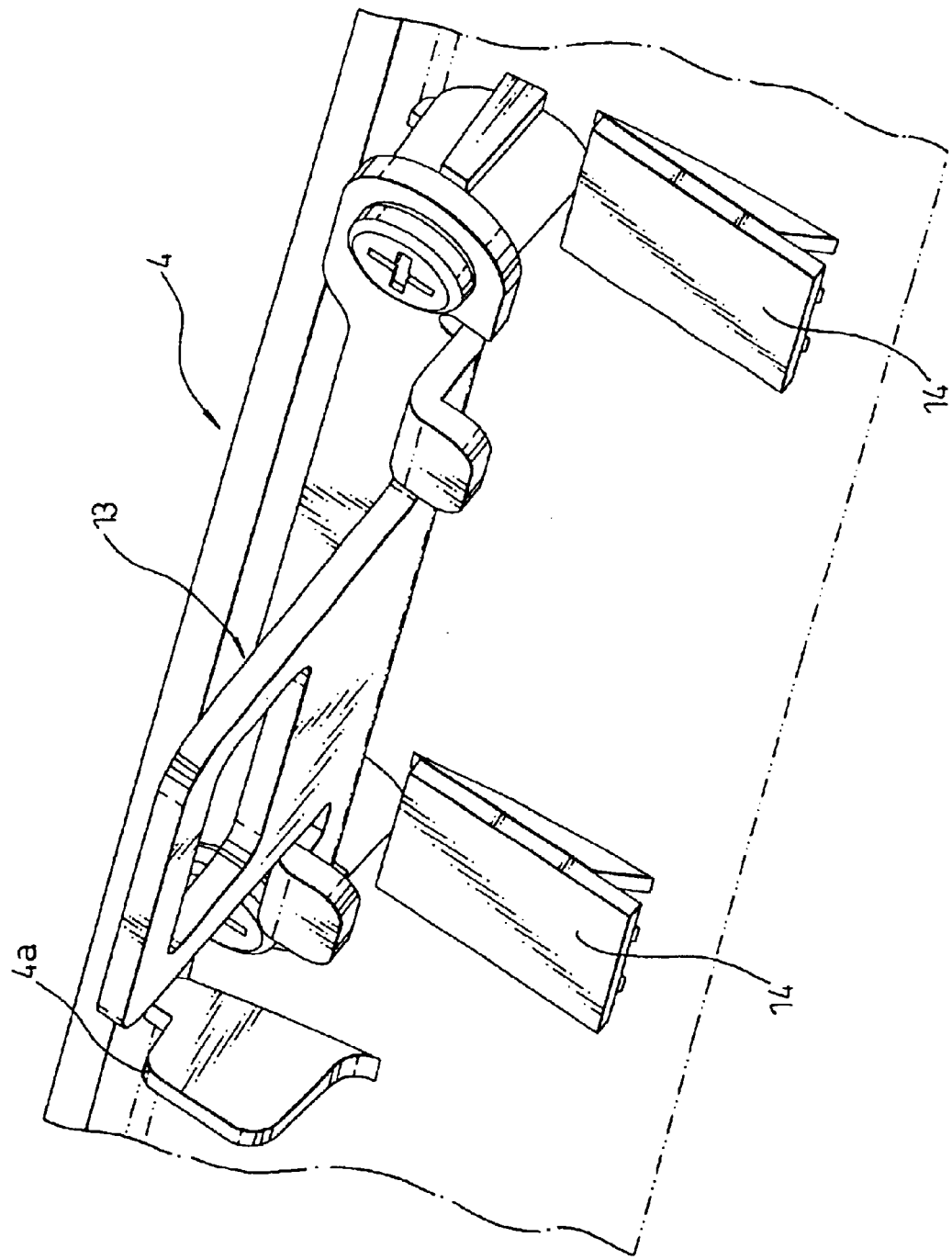
FIG. 8 is a perspective view showing a state in which the upper center fixing member is fixed to the back cover.
Figure 9:
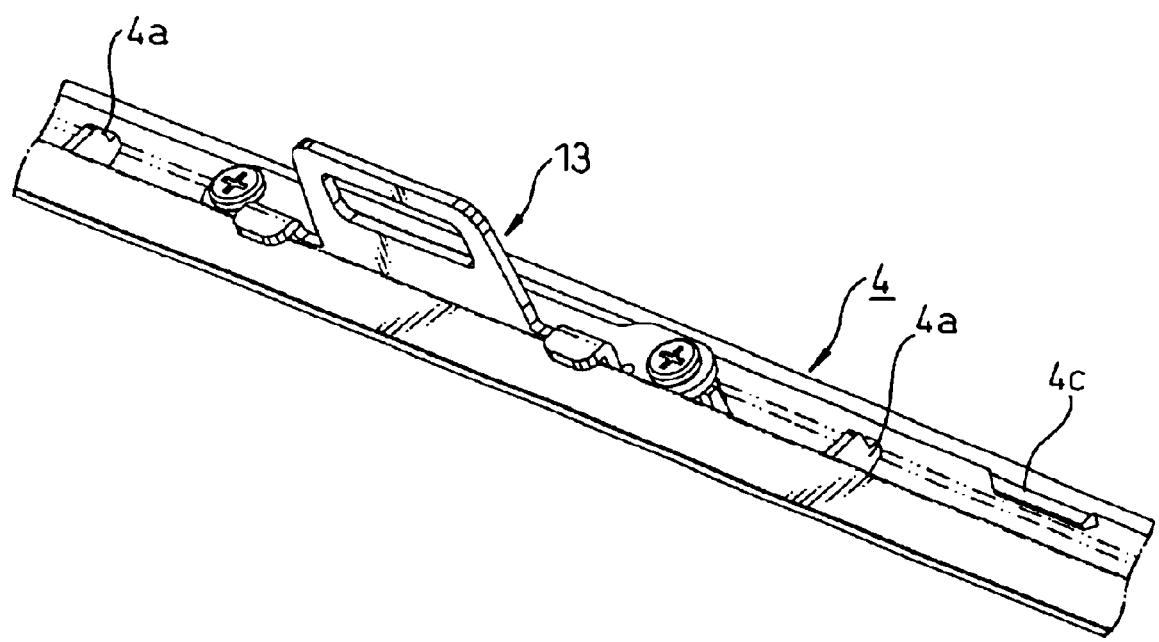
FIG. 9 is a perspective view showing a state in which the plane display unit is fixed with the upper center fixing member.

FIG. 8 is a perspective view showing a state in which the upper center fixing member 13 is fixed to the back cover 4, and FIG. 9 is a perspective view showing a state in which an upper central area of the plane display unit 5 is fixed with the upper center fixing member 13.

Sheets 14 are provided on the back cover 4 at positions opposite to the pair of claws 13c when the upper center fixing member 13 is mounted thereto. The sheet 14 is made of an elastic material such as rubber. When the plane display unit 5 is fixed to the back cover 4, the upper center fixing member 13 is attached to the back cover 4 with screws so that the upper central area of the plane display unit 5 is sandwiched between the pair of claws 13c of the upper center fixing member 13 and the pair of sheets 14.

Figure 10:
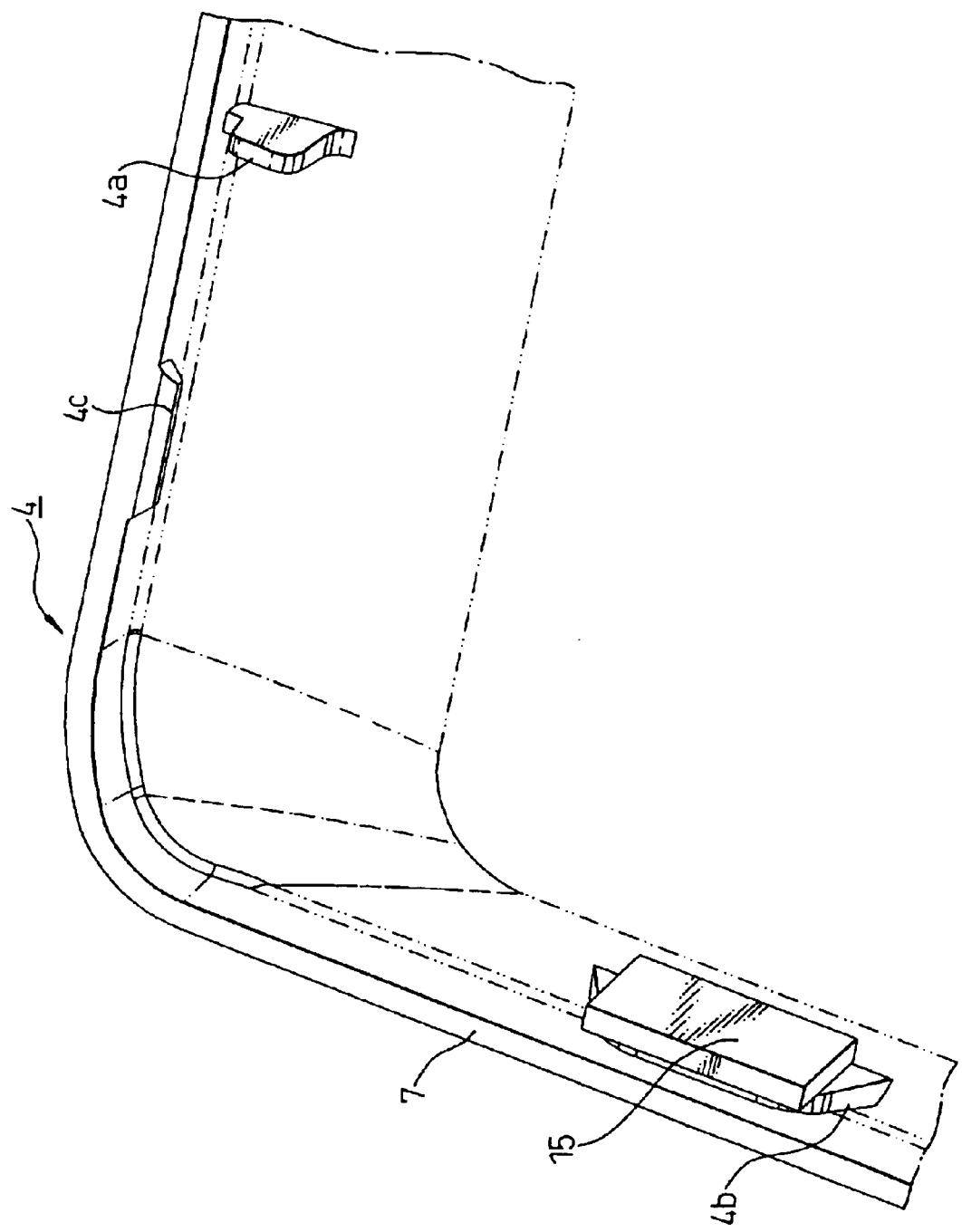
FIGS. 10 and 11 are perspective views, respectively, of an upper left portion of the back cover.
Figure 11:
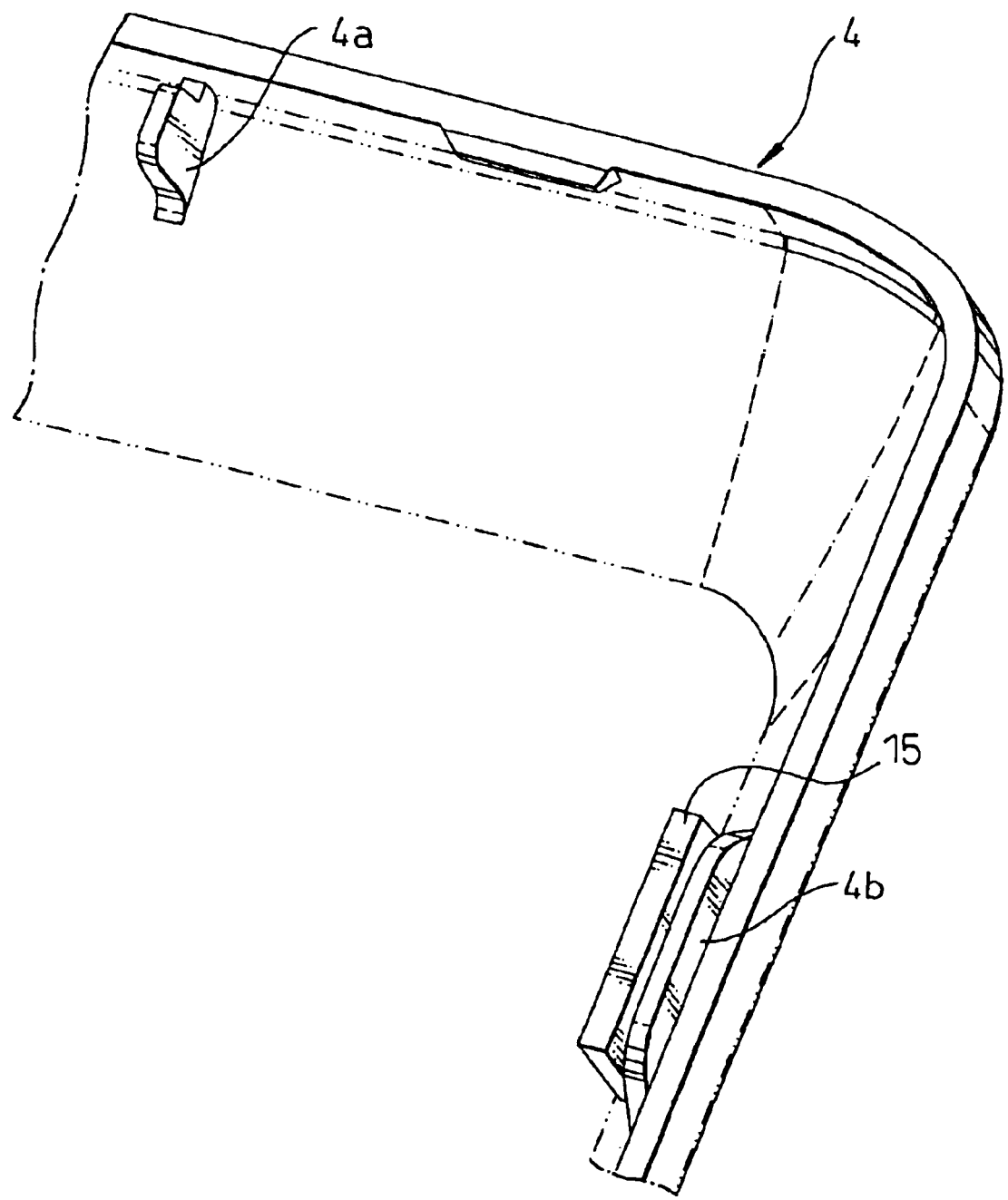

FIGS. 10 and 11 are perspective views of upper left and upper right areas of the back cover 4, respectively. As described before, the plurality of ribs 4a are provided at a distance in the upper end portion of the back cover 4 on the inside of the standing-up wall 9. These ribs 4a restrict the upward/downward position of the plane display unit 5. Also, the plurality of ribs 4b are provided generally parallel to the left and right side walls 7 and 8 at a distance on the inside of the left and right standing-up walls 7 and 8 on the left and right edges of the back cover 4.

Next, the procedure will be described for fixing the plane display unit 5 to the back cover 4 which is a housing and assembling the display 2 therewith.

Initially, the side fixing members 12 are fixed to the left and right surfaces of the plane display unit 5 with screws. At this time, the plurality of screw holes 12c of the side fixing members 12 are used. Shock absorbing members 15 (FIGS. 2 and 4(c)) are adhered to the left and right surfaces of the plane display unit 5 at positions corresponding to the ribs 4b closer to the upper surface than the side fixing member 12. The shock absorbing member may be a double-coated adhesive tape.

Next, this plane display unit 5 is fitted to the back cover 4 and the side fixing members 12 are fixed to the back cover 4 by screws. At this time, the screw holes 12d in the side fixing members 12 are used together with the screw holes 4e in the back cover 4 (FIG. 5).

Further, the upper central edge of the plane display unit 5 is fixed by the upper center fixing member 13. At this time, the screw holes 13a at the opposite ends of the upper center fixing member 13 are used together with the pair of screw holes 4f in the back cover 4 (FIG. 4). Accordingly, the upper central edge of the plane display unit 5 is fixed while being held between the pair of sheets 14 provided in the back cover 4 and the pair of claws 13c of the upper center fixing member 13.

In this regard, The positions of the left and right side surfaces of the plane display unit 5 are restricted by the ribs 4b provided on the inside of the standing-up walls 7 and 8 in the back cover while holding the double-coated adhesive tape 15 as the shock absorbing member between the both.

Also, the position of the upper surface of the plane display unit 5 is restricted by the ribs 4a provided on the inside of the standing-up wall 9 in the upper portion of the back cover. In such a manner, the position of the plane display unit 5 is restricted while front and rear surfaces thereof are held in a sandwiched manner.

Next, the front cover 6 is fitted onto the periphery of the plane display unit 5. The front cover 6 is made of proper resin, and the left and right edges and the upper surface are held by the engagement with the claws 4c provided on the inside of the standing-up walls 7 and 8 on the left and right edges and of the standing-up wall 9 on the upper surface of the back cover 4. For this purpose, claws 6b (FIG. 4(b)) engageable with the claws 4c are provided at positions corresponding to the claws 4c. The lower surface of the front cover 6 is fixed to the back cover 4 via hinge members 16.

That is, the hinge member 16 has two holes and, by using an outer one 16a of them, is fixed in advance to the screw hole 4g of the back cover 4 (FIG. 5) by a screw. And, by using a screw-fixing hole 6a in the front cover 6, another screw is screwed into the screw hole 4h of the back cover 4 via the other hole 16b of the hinge member 16 to fasten the front cover 6 with the back cover 4 together with the hinge member 16.

In this regard, the hinge member 16 is used for imparting the display 2 of the portable type computer with a proper torque when it is made to rotate relative to the main body 1 to guarantee the smooth rotation and stoppage of the display 2 at a predetermined position.

In this regard, in FIG. 2, an insulation sheet 17 is used for attaching an inverter circuit (not shown) for switching a backlight of the plane display unit 5 ON.

Next, a second embodiment of the present invention will be described in detail with reference to FIGS. 12 to 23.

Figure 12:
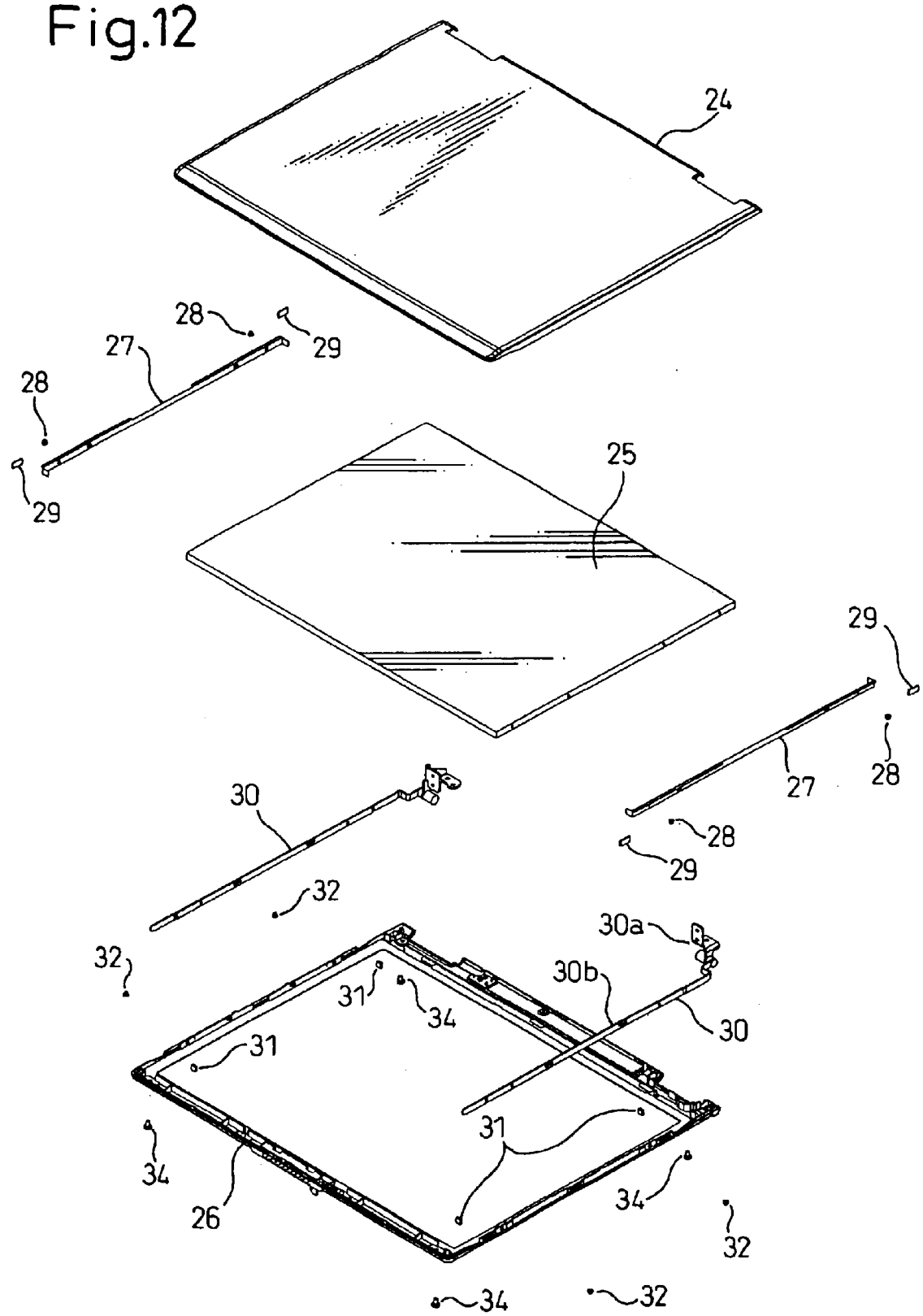
FIG. 12 is an exploded perspective view of the display in a portable type computer employing an attachment structure of a plane display unit according to a second embodiment of the present invention.

FIG. 12 is an exploded perspective view of the display in a portable type computer employing an attachment structure of a plane display unit according to a second embodiment of the present invention. Similarly to the first embodiment, the display of the second embodiment also includes a back cover 24 constituting a housing, a plane display unit 25 and a front cover 26.

As described later, support fittings 27 are attached to the plane display unit 25, and the support fittings 27 and cushion members 29 and 31 are held between the front cover 26 and the back cover 24 coupled by hinges 30. Thus, the plane display unit 25 is fixed.

Figure 13:
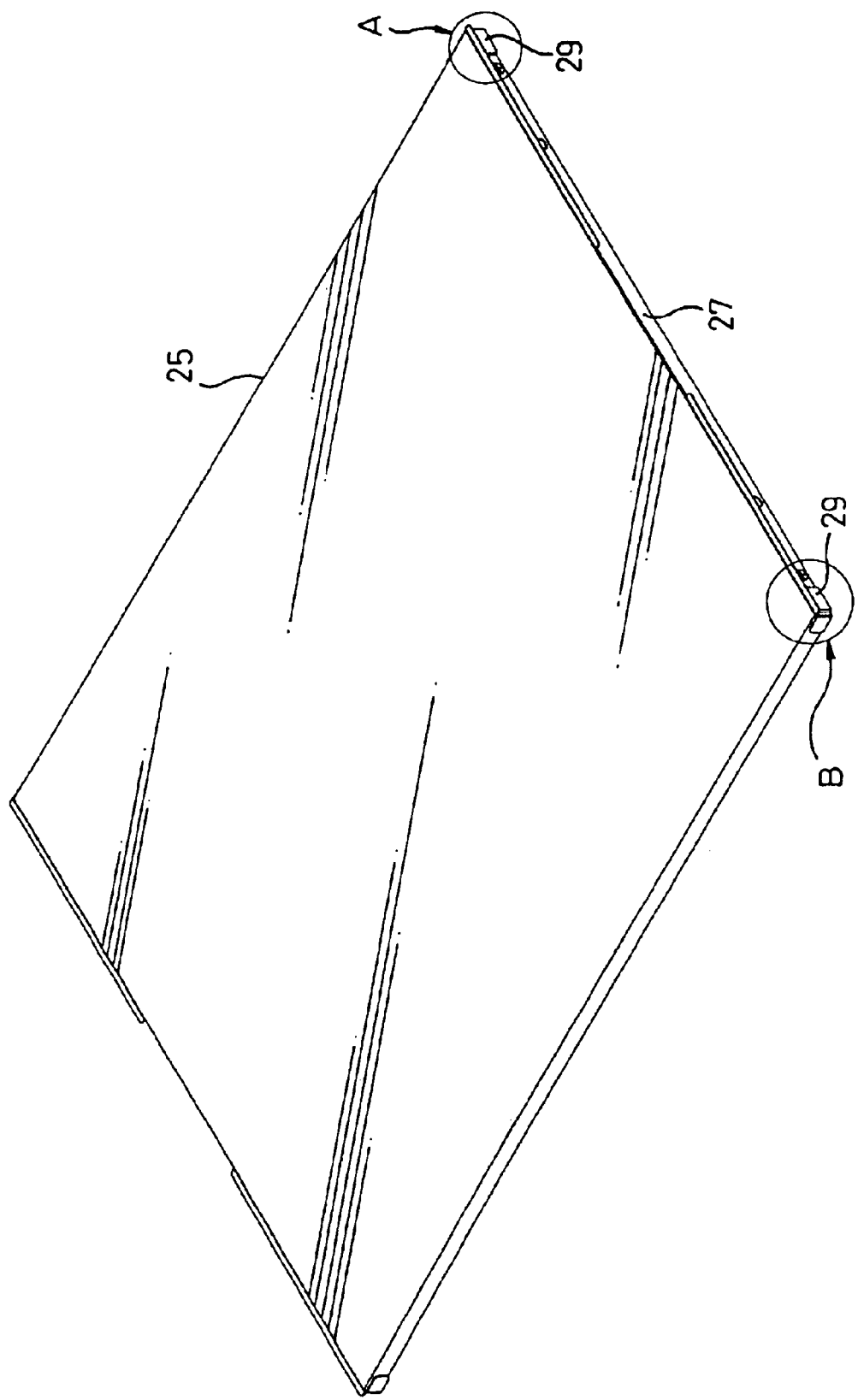
FIG. 13 is a perspective view showing a state in which support fittings 27 are attached to the respective sides of the plane display unit 25.
Figure 14:
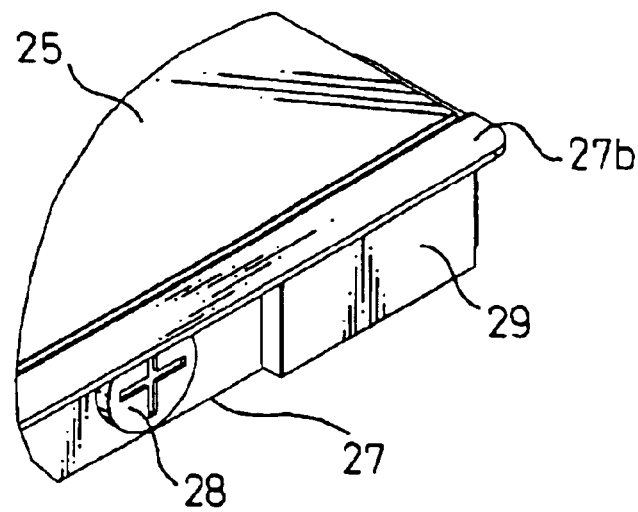
FIG. 14 is an enlarged perspective view of a part A in FIG. 13.
Figure 15:
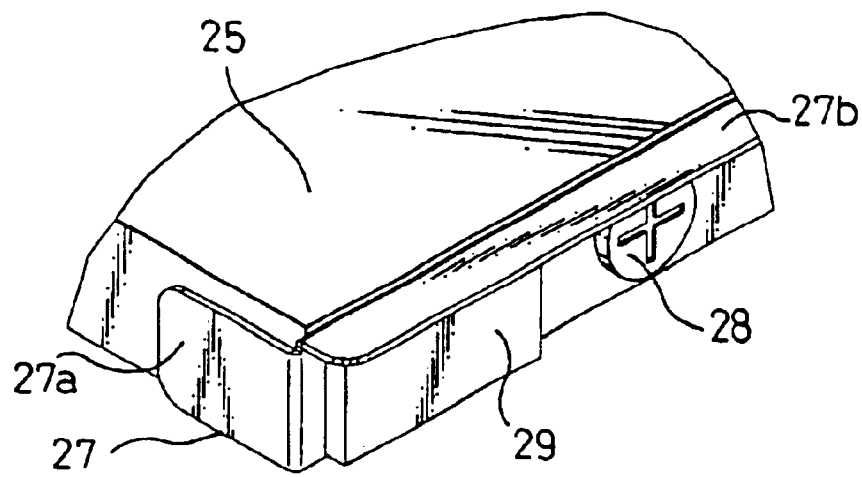
FIG. 15 is an enlarged perspective view of a part B in FIG. 13.

FIG. 13 is a perspective view illustrating a state in which the support fittings 27 are attached to both sides of the plane display unit 25. FIG. 14 is an enlarged perspective view of part A in FIG. 13, and FIG. 15 is an enlarged perspective view of part B in FIG. 13. The plane display unit 25 is of a flat rectangular shape as a whole in a similar manner as in the first embodiment, and has a pair of support fittings 27, 27 attached to opposite side surfaces thereof along a whole length thereof.

The respective fitting 27 is constituted by a strip-like plate having a length and a thickness approximately equal to those of the side surface of the plane display unit 25. Opposite ends of the fitting 27 are bent to form a bending portions 27a conforming with upper and lower surfaces of the plane display unit 25 (FIG. 15). Regarding the widthwise direction of the support fitting 27, one edge thereof has a bending portion 27b bent opposite to the bending portion 27a to have a smaller dimension (FIGS. 14 and 15). This bending portion 27b has a considerable length on the respective side thereof except for a central area as seen in the lengthwise direction of the fitting 27.

The respective fitting 27 is fixed to the side surface of the plane display unit 25 by means of screws 28 at two positions relatively near to opposite ends as seen in the lengthwise direction. In this opposite end portions, cushion members 29 are adhered to two positions, respectively, away outward from the positions of the screws 28. The cushion member 29 is of a generally rectangular shape having a width generally equal to that of the fitting 27. Also, it has a thickness smaller than the bending dimension of the bending portion 27b of the fitting 27b.

Figure 16:
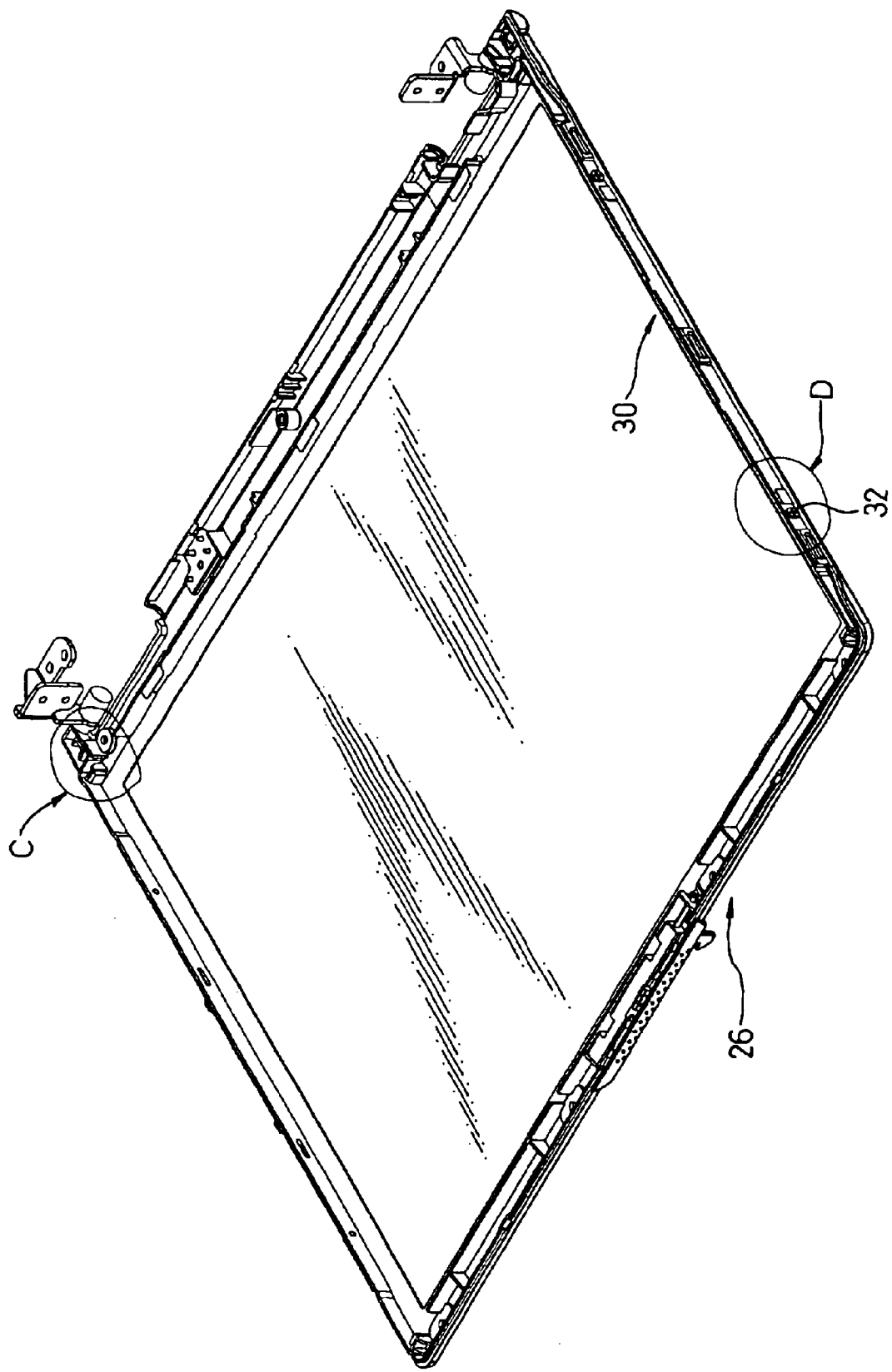
FIG. 16 is a perspective view showing a state in which hinges 30 are attached to the respective sides of a front cover 26.
Figure 17:
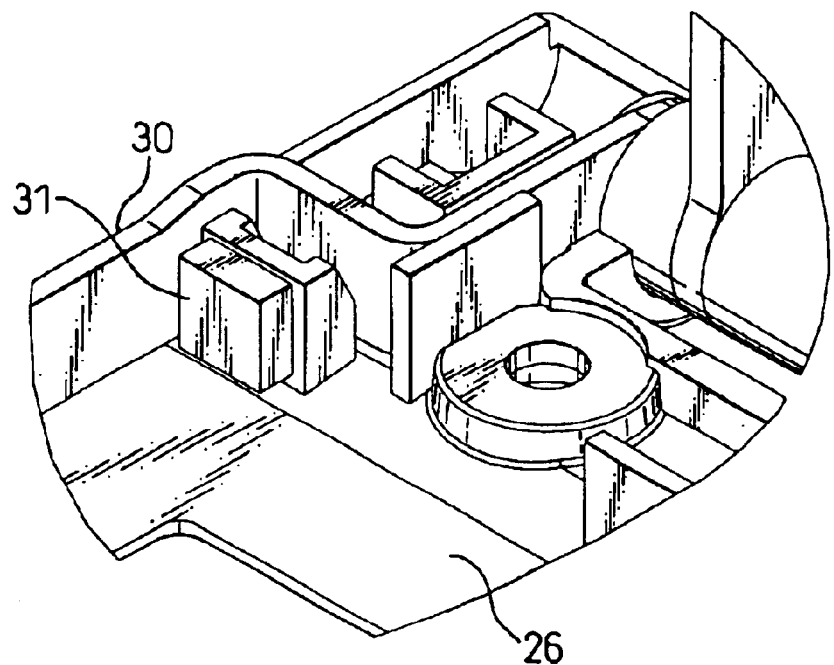
FIG. 17 is an enlarged perspective view of a part C in FIG. 16.
Figure 18:
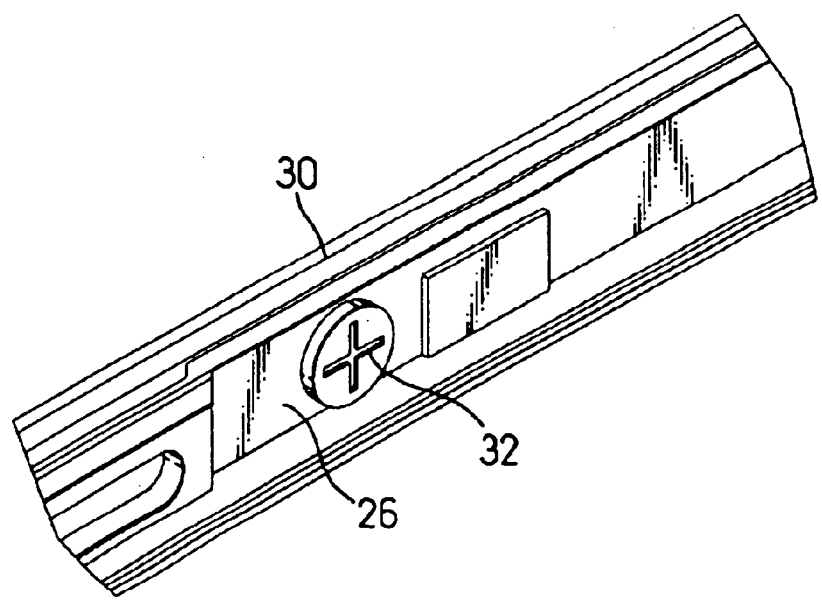
FIG. 18 is an enlarged perspective view of a part D in FIG. 16.

FIG. 16 is a perspective view showing a state in which the hinges 30 are attached to the both sides of the front cover 26. FIG. 17 is an enlarged perspective view of part C in FIG. 16, and FIG. 18 is an enlarged perspective view of part D in FIG. 16. The front cover 26 is of a frame shape, which outer line defines a rectangle slightly larger than the rectangular plane display unit 25 and which inner line defines a rectangle slightly smaller then the plane display unit 25.

On the other hand, the pair of hinges 30, 30 are attached to inside of wall portions provided on opposite sides of the front cover 26. Both the hinges 30, 30 are symmetrical with each other. The respective hinge 30 includes a hinge section 30a for constituting the hinge for enabling the display of this computer to open/close relative to the main body, and an arm 30b extending from the hinge section 30a while being integral therewith and having a length corresponding to the side of the front cover 26.

The hinge 30 is fixed to the inside of the side wall of the front cover 26 at two positions apart at a distance from each other in the lengthwise direction of the arm 30b. For this purpose, the front cover 26 has a standing-up wall along the outer circumference thereof. In the vicinity of the proximal portion of the hinges 30, as shown in FIG. 17, cushion members 31 are adhered, with which a lower surface of the plane display unit 25 is brought into contact. On the other hand, other cushion members 31 to be brought into contact with the upper surface of the plane display unit 25 are adhered to the front cover 26 side (FIG. 12). The cushion members 31 are four in total and in contact with both sides of the upper and lower surfaces of the plane display unit 26 to elastically hold the plane display unit 25 in the forward/rearward direction.

Figure 19:
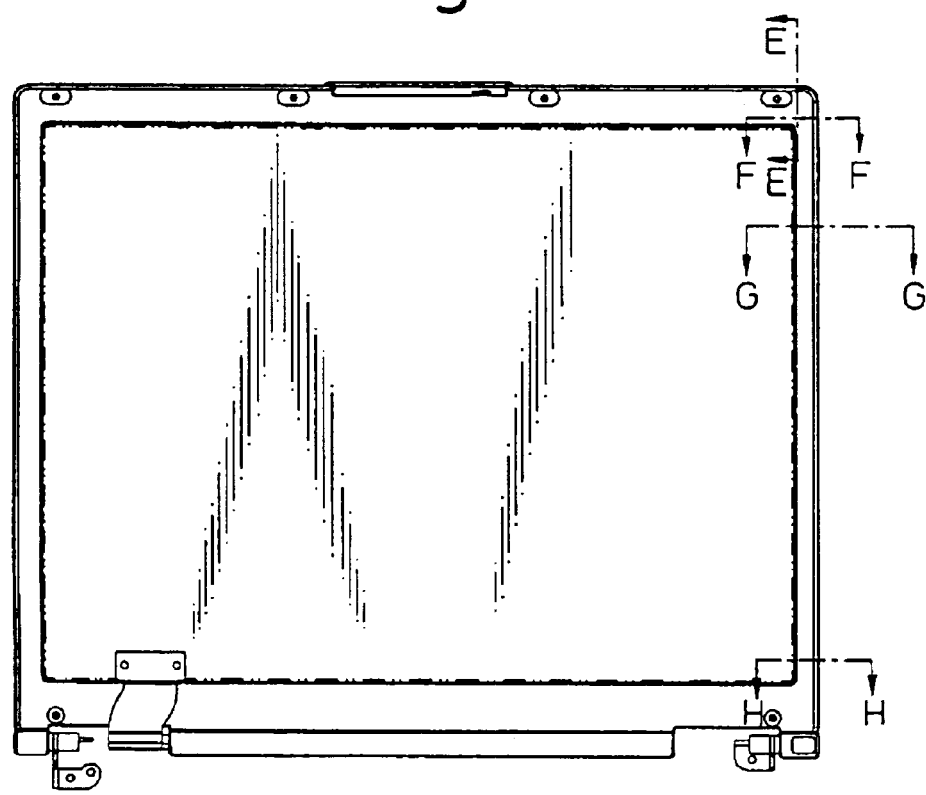
FIG. 19 is a plan view showing a state in which the plane display unit is fixed while being sandwiched between the back cover and the front cover.
Figure 20:
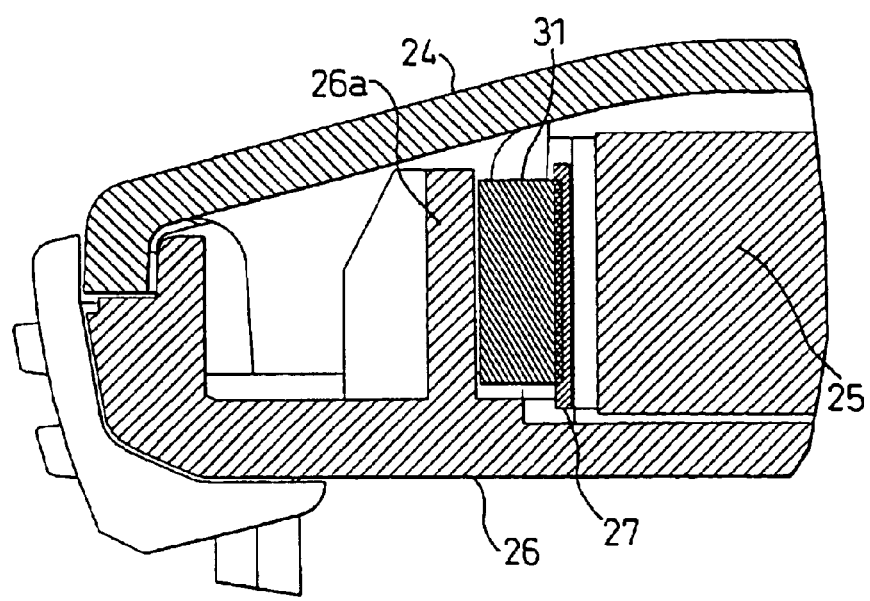
FIG. 20 is an enlarged sectional view taken along a line E—E in FIG. 19.
Figure 21:
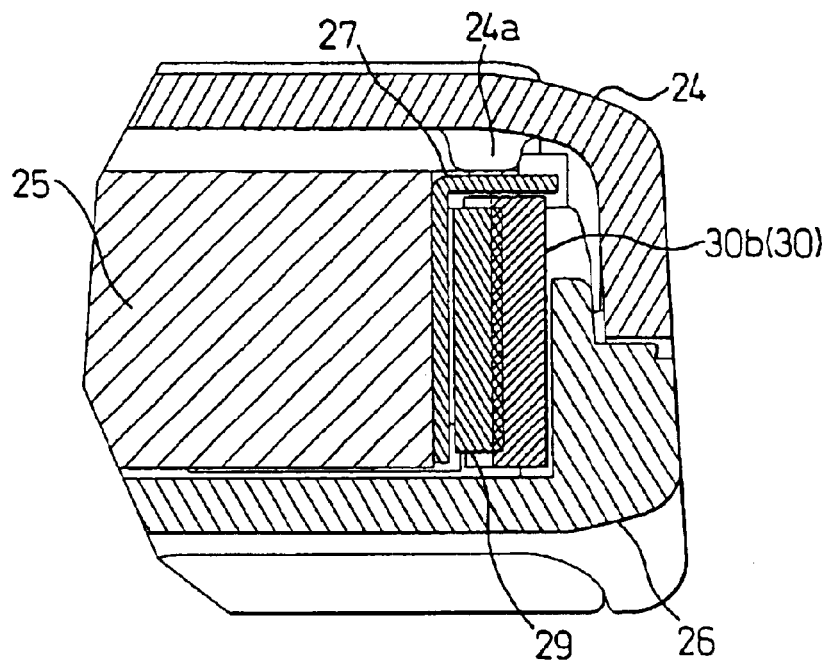
FIG. 21 is an enlarged sectional view taken along a line F—F in FIG. 19.
Figure 22:
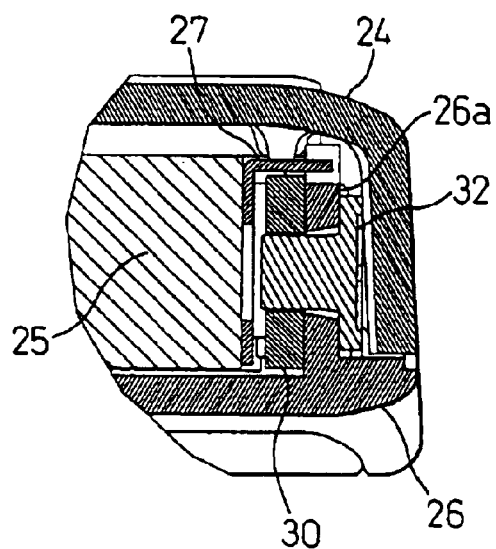
FIG. 22 is an enlarged sectional view taken along a line G—G in FIG. 19.

FIG. 19 is a plan view showing a state in which the plane display unit 25 is fixed in a sandwiched manner between the back cover 24 and the front cover 26. FIG. 20 is an enlarged sectional view taken along a line E—E in FIG. 19. FIG. 21 is an enlarged sectional view taken along a line F—F in FIG. 19, FIG. 22 is an enlarged sectional view taken along a line G—G in FIG. 19, and FIG. 23 is an enlarged sectional view taken along a line H—H in FIG. 19.

In FIG. 20, while the plane display unit 25 is sandwiched between the back cover 24 and the front cover 26, the cushion member 31 is interposed between the upper surface of the plane display unit 25 (the bending portion 27a in the support fitting 27 shown in FIG. 15) and a standing-up wall 26a of the front cover 26, and similarly, the cushion member 31 is interposed between the lower surface of the plane display unit 25 (the opposite bending portion 27a in the support fitting 27), whereby the plane display unit 25 is held via the cushion members 31 in the upward/downward direction. As described before, the cushion members 31 are provided at two positions in the vicinity of the left and right ends of the upper and lower surfaces of the plane display unit 25 and at four positions in total on the upper and lower sides of the plane display unit 25.

In FIG. 21, the cushion member 29 is also interposed between the side surface of the plane display unit 25 (support fitting 27) and the arm 30b of the hinge 30 while the plane display unit is fixed between the back cover 24 and the front cover 26 in a sandwiched manner. The cushion members 29 are provided at two positions in the vicinity of the upper and lower ends of the side surfaces of the plane display unit 25 and at four positions in total on the left and right sides of the plane display unit 25, as described before.

The fixation of the plane display unit 25 in the thickness direction thereof is carried out in such a manner that a ribs 24 of the back cover 24 is brought into contact with the bending portion of the 27b of the support fitting 17 to push plane display unit 25 toward the front cover 26. The rib 24a is formed in the inside wall of the back cover 24 in correspondence to a length of the bending portion 27b of the support fitting 27. In this regard, the fixation between the back cover 24 and the front cover 26 is carried out as shown in FIG. 12 by fastening the four corners of the rectangular front cover 26 to the back cover 24 with screws.

In FIG. 22, a state is illustrated, in which the hinge 30 is attached to the front cover 26 by means of a screw 32. The hinge 30 is fixed at two positions apart from each other in the lengthwise direction of the hinge 30 by fastening the screws 32 from the outside of the standing-up wall 26a of the front cover 26. The pair of left and right hinges 30, 30 are symmetrical in shape with each other and attached to the outside of the front cover 26 along the opposite standing-up walls 26a.

In FIG. 23, a state is illustrated in which the support fitting 27 is attached to the plane display unit 25 with the screw 28. As shown, the fitting 27 is fastened to the side surface of the plane display unit 25 at two positions apart from each other in the lengthwise direction with the screws 28 as described before. The pair of support fittings 27, 27 have the same shape and are fixed to the respective side surfaces of the plane display unit 25.

The display 2 (FIG. 1) is formed by fixing the plane display unit 25 between the back cover 24 and the front cover 26 in a sandwiched manner and coupled to the main body 1 by mounting the hinges 30 to the main body 1 of the portable type computer 1 (FIG. 1).

FIG. 24 shows a further embodiment which is the modification of the second embodiment according to the present invention, in which a hinge 30 having no arm and a front cover are illustrated.

That is, according to the second embodiment, each of the pair of hinges 30 and 30 includes a hinge section 30a forming the hinge capable of opening/closing the display of the computer relative to the main body, and an arm 30 extending from the hinge section 30a integral therewith and having a length corresponding to a side of the front cover 26. However, the hinge 30' shown in FIG. 24 has no arm extending along the side of the front cover 26 but has a section solely having a function for making the display to be openable/closable relative to the main body.

Accordingly, the hinge 30' shown in FIG. 24 does not require the screws 32 for fixing the arm 30b to the side of the front cover 26. This hinge 30' is fixed to the main body of the computer (not shown) on one hand, and fixed to the front cover 26 or the back cover 24 on the other hand. While there is no detailed illustration of this fixing method, a hole is provided in the hinge 30' for fixing the same and a screw hole is provided in the front cover 26 or the back cover 24, into which a screw not shown is screwed through the hole in the hinge.

As described above, the present invention has been described based on the preferred embodiments with reference to the attached drawings. The present invention should not be limited to the above-mentioned embodiments but may includes various changes and modifications thereof within a spirit or scope of the present invention.

Capability of Exploitation in Industry

As described hereinabove, according to the first embodiment of the present invention, since a structure is provided for fixing the plane display unit to the housing which is the back cover so that the left and right edges of the plane display unit are fastened via screws and the upper central edge is sandwiched between the back and front surfaces, no space is needed between the plane display unit and the housing for fixing the plane display unit, whereby the small-sizing of the apparatus is achievable.

Also, since the plane display unit is fixed at the upper central edge thereof, there is no need for providing the side fixing members for the left and right edges along a whole length of the plane unit. A problem regarding the strength can be solved by the provision of the upper center fixing member. Thereby, it is possible to reduce both of the production cost and weight of the plane unit structure.

Also, according to the second embodiment of the present invention, since the plane display unit 25 is fixed due to the elasticity of the cushion member instead of the direct screwing to the back cover or the front cover, it is possible to absorb or mitigate a strain applied to the plane display unit.

What is claimed is:

1. A plane unit structure for fastening a rectangular plane unit to a housing at three positions; left and right side edges and an upper central edge; wherein side fixing members are fixed to left and right edge surfaces of the plane unit with screws, and wherein the side fixing members are fixed to the housing with screws and the upper central edge of the plane unit is fastened to the housing while being sandwiched between back and front surfaces thereof.

2. A plane unit structure as defined by claim 1, wherein the back surface of the upper central edge of the plane unit is brought into contact with sheets fixed to the housing, and the front surface thereof is brought into contact with claws of an upper center fixing member fixed to the housing, so that the upper central edge is fixed between the both in a sandwiched manner.

3. A plane unit structure as defined by claim 2, wherein the sheet is formed of an elastic member.

4. A plane unit structure as defined by claim 2, wherein the upper center fixing member is provided with a hook portion of a portable type computer comprising a main body and a display having a plane unit openable/closable relative to the main body so that when the display is closed relative to the main body, the display is engaged with the main body by the engagement of the hook portion in the display with an engagement portion in the main body.

5. A plane unit structure as defined by claim 4, wherein the hook portion has an opening formed in the upper center fixing member, and the display is engaged with the main body by the engagement of the opening with a claw portion defining the engagement portion in the main body.

6. A plane unit structure as defined by claim 2, wherein the upper center fixing member has fixing holes at two positions apart from each other in the direction parallel to the upper edge of the plane unit and fixed to the housing with screws through the fixing holes.

7. A plane unit structure as defined by claim 4, wherein the claws are provided at two positions apart from each other in the direction parallel to the upper edge of the plane unit, and the hook portion is formed between the two claws.

8. A plane unit structure as defined by claim 2 wherein the sheets are provided at two positions opposite to the two claws, respectively.

9. A plane unit structure as defined by claim 1, wherein the side fixing member is an L-shaped member comprising a strip portion extending along each of left and right edge surfaces of the plane unit and a flat proximal end portion which is part of the strip portion exceeding the lower end of each of the left and right edge surfaces and bending from the strip portion at a right angle.

10. A plane unit structure as defined by claim 9, wherein the strip portion of the side fixing member is fixed to each of the left and right edge surfaces with screws at a plurality of positions along each of the left and right edge surface, and the flat portion is fixed to the housing with a screw at one position.

11. A plane unit structure as defined by claim 9, wherein the side fixing member is made of metal having elasticity.

12. A plane unit structure as defined by claim 11, wherein a distal end portion of the side fixing member opposite to the proximal end portion is apart from each of the left and right edge surfaces of the plane unit and brought into elastic contact with an inner wall surface of the housing.

13. A plane unit structure as defined by claim 9, wherein a shock absorbing member is provided between the strip portion of the side fixing member and the inner wall of the housing.

14. A plane unit structure as defined by claim 13, wherein the shock absorbing member is made of metal having the elasticity.

15. A portable type computer comprising a main body and a display which is a plane unit openable/closable relative to the main body, wherein the display comprises a housing and a rectangular plane unit, and side fixing members are fixed to left and right edge surfaces of the plane unit, respectively, with screws, and wherein the side fixing members are fixed to the housing with screws and an upper central edge of the plane unit is fixed to the housing while front and back surfaces thereof are sandwiched.

16. A portable type computer as defined by claim 15, wherein the display is provided with a frame-like front cover mounted along the outer periphery of the rectangular plane unit to sandwich the plane unit between the front cover and the housing.

17. A portable type computer as defined by claim 15, wherein a plurality of ribs are provided integral with the plane unit between the upper edge surface of the plane unit and the inner wall surface of the housing along the upper surface of the plane unit.

18. A plane unit stricture for fixing a rectangular plane unit while sandwiching opposite surfaces thereof in the thickness direction between a front cover and a back cover, wherein fittings are attached to side surfaces of the plane unit with screws and cushion members are brought into contact with the fittings so that the upper and lower surfaces or the left and right side surfaces of the plane unit are fixed to the cover via the cushion members.

19. A plane unit structure as defined by claim 18, wherein two of the fittings are attached to the left and right side surfaces of the plane unit, respectively.

20. A plane unit structure as defined by claim 19, wherein the fitting is formed of a strip having a width approximately equal to a thickness of the plane unit, which strip has a pair of bending portions at opposite ends thereof bent to be in contact with the upper or lower surface of the plane unit.

21. A plane unit structure as defined by claim 20, wherein two of the cushion members are adhered to the fitting fixed to the side surface of the plane unit at positions in the vicinity of opposite ends of the fitting in the lengthwise direction thereof, and further two of the cushion members are disposed at positions outside of the pair of bending positions.

22. A plane unit structure as defined by claim 21, wherein the fitting is fixed to the side surface of the plane unit with screws at two positions in the vicinity of lengthwise ends thereof, and the cushion members are adhered to the fitting at an end position closer to the screw-fixed position.

23. A plane unit structure as defined by claim 19, wherein the fitting has second bending portions at positions on one side in the widthwise direction bent away from the plane unit, and wherein these second bending portions are provided at opposite ends except for a central area in the lengthwise direction of the fitting, to be brought into contact with ribs provided in the front cover when the plane unit is sandwiched between the front and back covers.

24. A plane unit structure as defined by claim 18, wherein a pair of hinge arms are fixed to left and right sides of the front cover with screws, and the cushion members are interposed between the fitting fixed to the side surface of the plane unit and hinge arm.

25. A plane unit structure as defined by claim 24, wherein the hinge arm is fixed to a standing-up wall provided along the periphery of the rectangular frame-like front cover at front and back two positions with screws.

26. A portable type computer comprising a main body and a display provided with a plane unit openable/closable relative to the main body; the display comprising a rectangular plane unit, opposite surfaces of which are sandwiched between front and back covers as seen in the thickness direction, wherein fittings are attached to side surfaces of the plane unit, and cushion members are provided to be in contact with the fittings so that the upper or lower surface or the left or right surface of the plane unit is fixed to the cover.

27. A portable type computer as defined by claim 26, wherein a pair of hinge arms are fixed to left and right sides of the front cover with screws, and the cushion member is interposed between the fitting fixed on the side surface of the plane unit and the hinge arm, and wherein a proximal end portion of the hinge is fixed to the main body of the apparatus so that the display is openable/closable relative to the main body of the display.

28. A portable type computer as defined by claim 26, wherein a pair of hinges are provided on opposite sides of the plane display unit, and each of the hinges is fixed to the main body with a screw on one hand, and to the front or back cover on the other hand, so that the plane display unit is openable/closable relative to the main body.

29. A display unit which includes plane unit structure for fastening a rectangular plane unit to a housing at three position; left and right side edges and an upper central edge; wherein side fixing members are fixed to left and right edge surfaces of the plane unit with screws, and wherein the side fixing members are fixed to the housing with screws and the upper central edge of the plane unit is fastened to the housing while being sandwiched between back and front surfaces thereof.

30. A display unit as defined by claim 29, wherein the back surface of the upper central edge of the plane unit is brought into contact with sheets fixed to the housing, and the front surface thereof is brought into contact with claws of an upper center fixing member fixed to the housing, so that the upper central edge is fixed between the both in a sandwiched manner.

31. A display unit as defined by claim 30, wherein the sheet is formed of an elastic member.

32. A display unit as defined by claim 30, wherein the upper center fixing member has fixing holes at two positions apart from each other in the direction parallel to the upper edge of the plane unit and fixed to the housing with screws through the fixing holes.

33. A display unit as defined by claim 30, wherein the sheets are provided at two positions opposite to the two claws, respectively.

34. A display unit as defined by claim 29, wherein the side fixing member is an L-shaped member comprising a strip portion extending along each of left and right edge surfaces of the plane unit and a flat proximal end portion which is part of the strip portion exceeding the lower end of each of the left and right edge surfaces and bending from the strip portion at a right angle.

35. A display unit as defined by claim 34, wherein the strip portion of the side fixing member is fixed to each of the left and right edge surfaces with screws at a plurality of positions along each of the left and right edge surface, and the flat portion is fixed to the housing with a screw at one position.

36. A display unit as defined by claim 34, wherein the side fixing member is made of metal having elasticity.

37. A display unit as defined by claim 36, wherein a distal end portion of the side fixing member opposite to the proximal end portion is apart from each of the left and right edge surfaces of the plane unit and brought into elastic contact with an inner wall surface of the housing.

38. A display unit as defined by claim 34, wherein a shock absorbing member is provided between the strip portion of the side fixing member and the inner wall of the housing.

39. A plane unit structure as defined by claim 38, wherein the shock absorbing member is made of metal having elasticity.

40. A display unit which includes a plane unit structure for fixing a rectangular plane unit while sandwiching opposite surfaces thereof in the thickness direction between a front cover and a back cover, wherein fittings are attached to side surfaces of the plane unit with screws and cushion members are brought into contact with the fittings so that the upper and lower surfaces or the left and right side surfaces of the plane unit are fixed to the cover via the cushion members.

41. A display unit as defined by claim 40, wherein two of the fittings are attached to the left and right side surfaces of the plane unit, respectively.

42. A display unit as defined by claim 41, wherein the fitting is formed of a strip having a width approximately equal to a thickness of the plane unit, which strip has a pair of bending portions at opposite ends thereof bent to be in contact with the upper or lower surface of the plane unit.

* * * * *

UNITED STATES PATENT AND TRADEMARK OFFICE
CERTIFICATE OF CORRECTION

PATENT NO.     : 6,989,986 B2
DATED          : January 24, 2006
INVENTOR(S)    : Kumagai et al.

It is certified that error appears in the above-identified patent and that said Letters Patent is hereby corrected as shown below:

<u>Title page,</u>
Item [56], References Cited, U.S. PATENT DOCUMENTS, add the following references:
-- 2002/0064036   May 30, 2002      Yano et al.
   6,594,143      July 15, 2003     Yano et al. --.
FOREIGN PATENT DOCUMENTS, add the following references:
-- 478603         Mar. 1, 2002      Taiwan
   331943         May 11, 1998      Taiwan --.

<u>Column 12,</u>
Line 28, delete "having the" insert -- having --.

Signed and Sealed this

Twenty-fifth Day of April, 2006

JON W. DUDAS
*Director of the United States Patent and Trademark Office*